United States Patent
Zhang et al.

(10) Patent No.: US 10,471,054 B2
(45) Date of Patent: Nov. 12, 2019

(54) CDK1 INHIBITORS OF ACETYL CHRYSIN MANNICH BASE DERIVATIVES, SYNTHESIS AND USE THEREOF

(71) Applicant: Fan Zhang, Dalian, Liaoning (CN)

(72) Inventors: Fan Zhang, Liaoning (CN); Shixuan Zhang, Liaoning (CN); Xiulan Ju, Liaoning (CN)

(73) Assignee: Fan Zhang, Dalian, Liaoning (CN)

( * ) Notice: Subject to any disclaimer, the term of this patent is extended or adjusted under 35 U.S.C. 154(b) by 0 days.

(21) Appl. No.: 16/219,066

(22) Filed: Dec. 13, 2018

(65) Prior Publication Data

US 2019/0216792 A1 Jul. 18, 2019

Related U.S. Application Data

(63) Continuation-in-part of application No. PCT/CN2017/087864, filed on Jun. 12, 2017.

(30) Foreign Application Priority Data

Jun. 15, 2016 (CN) .......................... 2016 1 0427354

(51) Int. Cl.
| | |
|---|---|
| *A61K 31/453* | (2006.01) |
| *A61K 31/353* | (2006.01) |
| *A61K 31/4025* | (2006.01) |
| *A61K 31/541* | (2006.01) |
| *A61K 31/5355* | (2006.01) |
| *A61K 31/496* | (2006.01) |

(52) U.S. Cl.
CPC .......... *A61K 31/453* (2013.01); *A61K 31/353* (2013.01); *A61K 31/4025* (2013.01); *A61K 31/496* (2013.01); *A61K 31/5355* (2013.01); *A61K 31/541* (2013.01)

(58) Field of Classification Search
CPC .................................................... A61K 31/453
USPC .......................................................... 549/402
See application file for complete search history.

(56) References Cited

PUBLICATIONS

Mohammed et al., Nat. Prod. Comm. (2011), 6(1), pp. 31-34.*

\* cited by examiner

*Primary Examiner* — Taofiq A Solola
(74) *Attorney, Agent, or Firm* — Novick, Kim & Lee, PLLC; Alllen Xue

(57) ABSTRACT

Provided is a series of acetyl Chrysin Mannich base derivatives with the structures illustrated in the following scheme: wherein $R_1$ is acetyl and $R_2$ is cycloalkylamine-methyl, or $R_2$ is acetyl and $R_1$ is cycloalkylamine-methyl. Such derivatives are cyclin-dependent protein kinases 1 (CDK1) selective inhibitors. Base on the levels of $.O_2^-$ and $Fe^{++}$ are higher 5-15 times in cancer cells than in normal cells, the action mechanism of such derivatives by regulating intracellular reactive oxygen species (ROS) is activating mitochondria apoptosis pathway without the death receptor pathway, thus selectively inducing apoptosis of cancer cells and protecting normal cells. Inside, CH-j has a good druggability for the selectivity of solid cancers. Moreover, CH-f has also a good druggability for the systemic cancers.

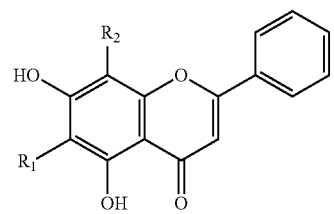

15 Claims, 11 Drawing Sheets

Figure 1:
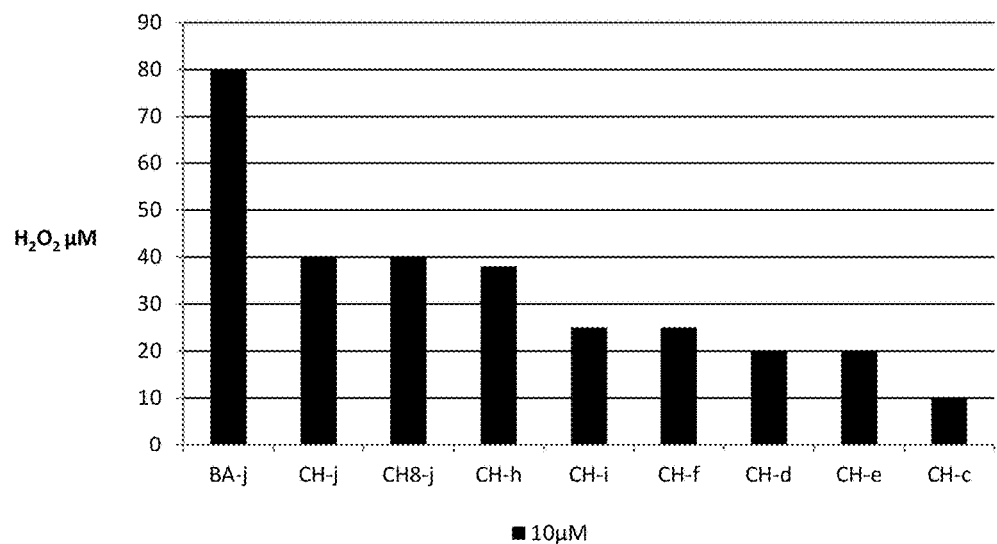

CDK1 INHIBITORS OF ACETYL CHRYSIN MANNICH BASE DERIVATIVES, SYNTHESIS AND USE THEREOF

CROSS-REFERENCE TO RELATED APPLICATIONS

The present application is a continuation-in-part (CIP) of PCT international patent application No. PCT/CN2017/087864 filed on Jun. 12, 2017, which claims priority to Chinese patent application No. 201610427354.3 filed on Jun. 15, 2016, the entire disclosures of which are hereby incorporated by reference.

FIELD OF THE INVENTION

The present invention relates to the field of drug synthesis. More particularly, it relates to synthesis of a series of acetyl Chrysin Mannich base derivatives, as Cyclin-dependent protein kinases 1 (CDK1) selective inhibitors, and their potential application especially in anti-solid cancers.

BACKGROUND OF THE INVENTION

Cyclin-dependent protein kinases (CDK) are same cell cycle regulation of key signaling molecules. Hartwell, Nurse and Hunt awarded the 2001 Nobel Prize for revealing CDK cell cycle control mechanisms. Uncontrolled cell cycle is one of the hallmarks of cancer, and CDK over activity leads to cell proliferation. Therefore, in recent years, the focus of the research and development of targeted anti-cancer drugs in the world has begun to shift to CDK inhibitors.

CDK4/6 inhibitor had been listed as Palbociclib of Pfizer (Ibrance, 2015), Ribociclib of Novartis (Kisqali, 2017) and Abemaciclib of Iilly (Verzenio, 2017). However, due to the weak anticancer effectives of the CDK4/6 inhibitors, need combined with other anticancer drugs such as Letrozole, and with same serious adverse reactions and drug resistance.

CDK1 is the only one that must be used in cell proliferation and has become the latest target of cancer drug research. [Nature, 2007, 448: 811-816] Therefore, CDK1 is targeted of the research and development of anti-cancer drugs. Flavonoids are same natural CDK1 selective inhibitors, widely exist in many fruits, vegetables and herbs, with many kinds of biological activity as anti-thrombotic, anti-inflammatory, immunity to normal, antiviral, anti-cancer, and so on. Flavonoids are not directly kill the cells, but based on the regulation of intracellular reactive oxygen species (ROS), thus selectively induce apoptosis, inhibit proliferative and metastasis of solid cancers by target activating intracellular apoptosis pathway and bypassing extrinsic death receptor pathway, and protecting normal cells. [Eur. J. Med. Chem., 2012, 49: 24-40]

There are different mechanisms of oxidation and reduction within normal cells and tumor cells. Proliferation and metastasis of solid cancers cells need a lot of oxygen. So, hypoxia is an important characteristic of solid cancers microenvironment. In normal cells, in the state of oxygen enrichment, a small amount of $.O_2^-$ is capturing by superoxide dismutase (SOD), with releasing $H_2O_2$, and decomposing by glutathione (GPX) and catalase (CAT). A small amount of 0.02" is capturing too by polyphenolic compounds (as flavonoids) similarly SOD, with releasing $H_2O_2$, and decomposing by GPX and CAT. In cancer cells by lacking SOD, GPX and CAT, in the lack of oxygen enrichment, a large amount of $.O_2^-$ is collecting with promoting the proliferation of cancer cells. A large amount of $.O_2^-$ is capturing by flavonoids with releasing and collecting $H_2O_2$, which high concentration of $H_2O_2$ can specific target oxidative the enzymes with active site of cysteine (such as CDC25, HIF-1α, caspase), thus activating mitochondria apoptosis pathway without the death receptor pathway, thereby, selectively inhibit proliferation and induce apoptosis of cancer cells. [Biomedicine & Pharmacotherapy, 2005, 59: 169-174; Cancer Letters, 2007, 252: 1-8]

However, due to flavonoids with poor solubility and the strong "liver first pass effect" and "hepatoenteral circulation" of glucose aldehyde acid metabolism (>95%) by oral, so that bioavailability of flavonoids is very low. Therefore, to improve druggability, based on the structure modification of flavonoids have an important practical value. [Eur. J. Pharmacology, 2010, 630: 121-130] The structure modifications of flavonoids by organic amines are most remarkable.

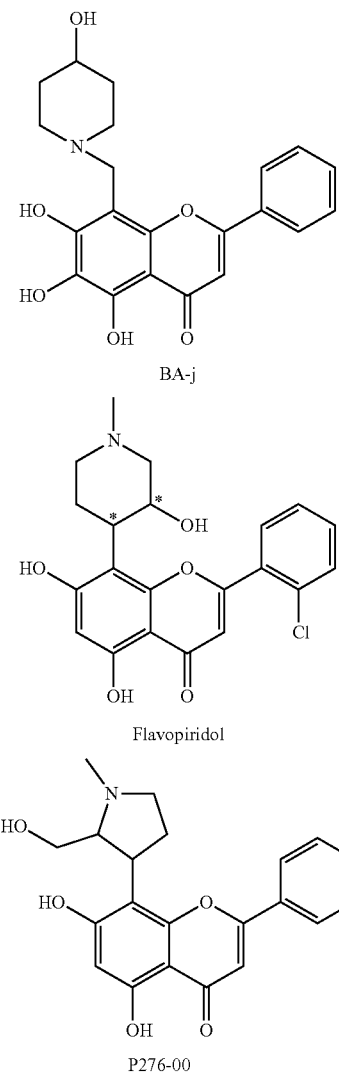

-continued

Voruciclib

In the structure modifications of flavonoids with general organic amine (no Mannich bases) substituent, as Flavopiridol, P276-00 and Voruciclib, due to do not format the stable six-member ring structure by intermolecular hydrogen bond between phenol hydroxyl and amine substituent, the "liver firs effect" by oral and "hepatoenteral circulation" cannot be effective inhibited with little bioavailability. Meanwhile, the flavonoids nucleus is not activated by substituent bases with druggability little excellent.

*Scutellaria baicalensis* is herb drug from Chinese with main active Baicalin, Baicalein as hydrolysis product of Baicalin is stronger anti-proliferation activity than Baicalin. [Cancer Treatment Reviews, 2009, 35: 57-68] Baicalein is an inhibitor of CDK1 with selectively inducing apoptosis of cancer cells with little toxic effect on normal cells by regulating ROS. [Eur J Pharmacology, 2010, 630: 121-130; Neuroscience Letters, 2008, 444: 264-269] So, Baicalein as a lead compound for structural modification is a great significance. The Mannich derivatives of Baicalein, a preparation method and thereof with the inhibition activity of protein kinase C, was public on CN1427003A. 8-aminemethyl-Baicalein Mannich derivatives, a preparation method and thereof with the inhibition activity of CDK1, was public on CN200910140275.4 and U.S. Pat. No. 8,377,895B2. 8-(4-hydroxy-piperidin-1-ylmethyl)-2-phenyl-chromen-4-one (BAj) is the best CDK1 selective inhibitor, and different from the cytotoxic drugs with damaging cancer cells also normal cells. By using the differential mechanisms of oxidation and reduction within normal cells, cancers cells and activated lymphocyte, BA-j can target activate intrinsic apoptosis pathway and pass extrinsic death receptor pathway, thus selectively induce apoptosis, inhibit proliferative of cancer cells and activated lymphocyte, and protect normal cells. The druggability of BA-j is excellent in the application. [Scientific Reports, 2015, 5: 13626; Anti-Cancer Agents in Medicinal Chemistry, 2016, 16: 914-924; Fitoterapia, 2015, 107: 36-34; RSC Advances, 2015, 5: 89818-89826; Bioorganic & Medicinal Chemistry, 2008, 16: 7127-7132]

In structure modifications of BA-j by Mannich bases substituent, due to format the stable six-member ring structure by intermolecular hydrogen bond between phenolic hydroxyl and Mannich amine, the "liver firs pass effect" of glucose aldehyde acid metabolism (<5%) by oral and "hepatoenteral circulation" are effective inhibited, and bioavailability significantly improved. Due to log P of BA-j is lower, high protein binding rate and strong affinity, mainly distributed in the blood, so the blood system exceptions (such as metastasis cancer cell into blood, leukemia and AIDS) good effect of elimination of symptoms caused by abnormal immune.

Chrysin is also a natural flavonoid with extensive pharmacological activities, is one of the major components of propolis, and has the anticancer and radiotherapy sensitization, inhibit the aromatase activity, anti-inflammatory, anti-oxidation, the prevention and treatment of disease of heart head blood-vessel and other pharmacological effects. The inhibition of VEGF by HIF-1α can inhibit the formation of new blood vessels and selectively induce apoptosis of cancer cells and inhibit the metastasis of solid cancer [Molecular Cancer Therapeutics, 2007, 6: 220-226] Therefore, it is of great significance to modify the structure of Chrysin in order to obtain a new type of anti-solid cancers drug with high efficiency and low toxicity.

Flavopiridol is an organic amine derivative of Chrysin as the first generic CDKs inhibitor with significantly improving the sensitivity of chemotherapy drugs, at the same time also found that can prevent HIV-1 in cell proliferation, show the good prospects of cancer and AIDS. The subsequent application of chemotherapy can effectively improve the sensitivity of chemotherapy drugs and bring new ideas and hope to the treatment of cancer and AIDS. However, it is a pan-CDKs inhibitor. The solubility is poor, and the intravenous drip steady plasma concentration low (0.27 μM), by oral which resulted in a stronger "liver first pass effect" with low bioavailability. It is not easy to be degraded into tissue cells with producing strong cytotoxic effects and causing severe secretion of diarrhea and other adverse reactions. The druggability of Flavopiridol is not excellent. [Blood, 2009, 113: 2637-2644; Life Sciences, 1998, 62: 1861-1873; Invest New Drugs, 2012, 30: 629-638]

P276-00 is an organic amine derivative of Chrysin as a selective inhibitor of CDK 4, 1, 9 with the anticancer activity and drug potency superior to that of Flavopiridol, which had little effect on normal pulmonary fibroblasts, as wt-38 and MRC-5, and had entered phase III clinical stage. There is little diarrhea and other adverse reactions with comparing Flavopiridol. There is the similar druggability problem of Flavopiridol. [Molecular Cancer Therapeutics, 2007, 6: 918-925, 918-925; Leukemia, 2009, 23: 961-970]

Voriciclib of similar P276-00 is another organic amine derivative of Chrysin as a selective inhibitor of CDK 4, 1, 9. There are more than 30 types of cancer cell lines that show a more anticancer activity, and currently being treated with other drugs for melanoma. There is the similar druggability problem of P276-00 and Flavopiridol.

The substituent of Mannich base derivative of Chrysin on the existing technology had 6-aminemethyl, 8-aminemethyl, and 6,8-diaminemethyl [Synlett, 2006, (8): 1225-1229; Shenyang Pharmaceutical University J. , 2010, 27: 448-452; Nature Product Communications, 2011, 6: 31-34; Ukrainica Bioorganica Acta2, 2013, 3-7; Anti-Cancer Agents in Medicinal Chemistry, 2016, 16: 914-924] The anticancer activity of the Mannich base derivatives of Chrysin had a little improvement.

SUMMARY OF THE INVENTION

Contents of the Invention:

The aim of the present invention of a series of acetyl Chrysin Mannich base derivative is going to find a new type of CDK1 selective inhibitor with especially potential application in solid cancers with different from the existing technology.

Technical Solutions to Solve the Technical Problems of the Present Invention:

The invention is disclosed a series of acetyl Chrysin Mannich base derivatives with the structures illustrated in the following scheme: wherein $R_1$ is $CH_3CO$ and $R_2$ is cycloalkylamine-methyl, or $R_1$ is cycloalkylamine-methyl and $R_2$ is $CH_3CO$, only one is $CH_3CO$ in $R_1$ or $R_2$.

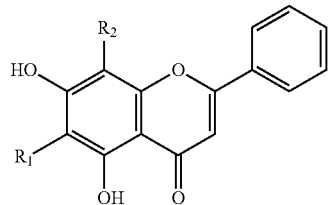

The cycloalkylamine-methyl in acetyl Chrysin Mannich base derivatives is pyrrolidinylmethyl, piperidinylmethyl, N-morpholinylmethyl, N-thiomorpholinylmethyl, N-methylpiperazinylmethyl, piperazinylmethyl, N-2'-hydroxyethylpiperazinylmethyl, 4'-piperidonylmethyl, 4'-hydroxylpiperidinylmethyl, 3'-hydroxypyrrolidinylmethyl, L-prolinolmethyl or D-prolinolmethyl.

acetyl-acetone, ethyl-acetoacetate or methyl-isobutyl-ketone.

The optimization of acetyl Chrysin Mannich base derivatives, wherein $R_1$ is $CH_3CO$ and $R_2$ is 4'-hydroxylpiperidinylmethyl, N-morpholinylmethyl, N-thiomorpholinylmethyl, N-2'-hydroxyethylpiperazinylmethyl or N-methylpiperazinylmethyl.

The further optimization of acetyl Chrysin Mannich base derivatives, wherein $R_1$ is $CH_3CO$ and $R_2$ is 4'-hydroxylpiperidinylmethyl or N-methylpiperazinylmethyl.

In one of the methods, the acetyl Chrysin in the above method is the starting material of 2, 4, 6-trihydroxy-acetophenone, which is condensed with phenylacetic-acid-ethyl-acetate. 6-acetyl-Chrysin and 8-(1-hydroxy-vinyl)-Chrysin by separating were obtained respectively. [J. Chem. Soc. Perkin Trans I, 1973, 503-505]

Specifically, the synthetic route of the synthesis method can be expressed as follows for 6-acetyl-5, 7-dihydroxy-8-(4-hydroxy-piperidin-1-ylmethyl)-2-phenyl-chromen-4-one (CH-j) and 8-(1-hydroxy-vinyl)-5, 7-dihydroxy-6-(4-hydroxy-piperidin-1-ylmethyl)-2-phenyl-chromen-4-one (is-CH-j).

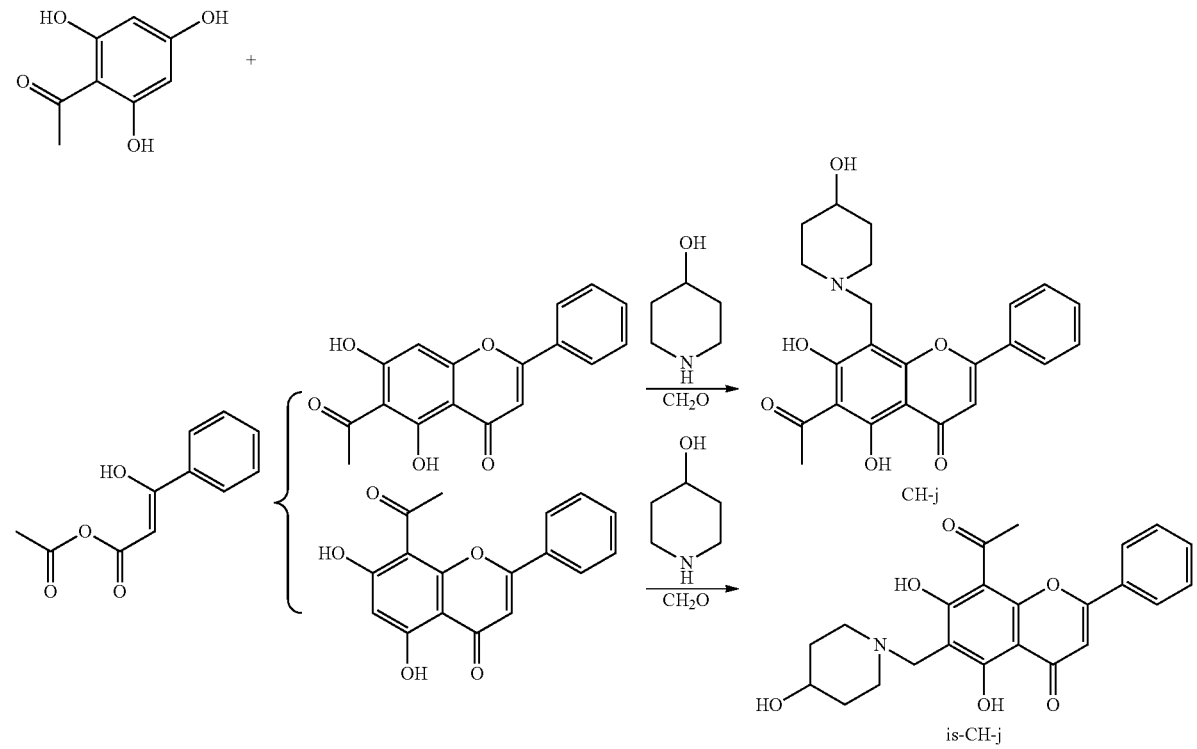

The synthesis process of Mannich base derivatives of acetyl Chrysin is as follows: taking 6-acetyl-Chrysin or 8-acetyl-Chrysin as lead compound in an organic solution, mixing it with formaldehyde solution and cycloalkylamine compound, stirring and heating by Mannich reaction, so as to get the products of the Mannich base derivatives of acetyl Chrysin.

In the process, the cycloalkylamine compound is pyrrolidine, piperidine, morpholine, sulfurmorpholine, 4-methylpiperazine, piperazine, 4-hydroxyethyl-piperazine, 4-piperidone, 4-piperidinol, 3-pyrrolidinol, L-prolinol or D-prolinol.

In the process, the organic solution is ethanol, acetonitrile, tetrahydrofuran, dioxane, ethyl-acetate, butyl-acetate, The present invention provides a series of acetyl Chrysin Mannich base derivative, with is a cyclin-dependent protein kinase 1 (CDK1) selective inhibitor. The action mechanism of the derivatives is regulation intracellular reactive oxygen species (ROS) and thus selectively induce tumor cell apoptosis, inhibit proliferative and metastasis of solid cancers, and protect normal cells. Due to format the stable six-member ring structure by intermolecular hydrogen bonds between phenolic hydroxyl and Mannich amine (or acetyl), the "liver firs effect" by oral and "hepatoenteral circulation" are effective inhibited with improving bioavailability significantly.

Such derivative has a good druggability by oral with unique pharmacokinetic properties, high efficiency and low toxicity, a clear mechanism of action, and a good selectivity for solid cancers. The derivatives have a rich source of raw materials, simple technology, high purity and low cost which this invention provides the application of Mannich base derivatives of acetyl Chrysin in the preparation of anticancer drugs with especially potential application in solid cancers.

Technical Effect

The abbreviations used in the present invention have 5, 6, 7-trihydroxy-8-(4-hydroxy-piperidin-1-ylmethyl)-2-phenyl-chromen-4-one (BA-j), 5, 6, 7-trihydroxy-8-(4-methylpiperazin-1-ylmethyl)-2-phenyl-chromen-4-one (BA-f), 6-acetyl-5, 7-dihydroxy-8-(4-hydroxy-piperidin-1-ylmethyl)-2-phenyl-chromen-4-one (CH-j), and 6-acetyl-5, 7-dihydroxy-8-(4-methylpiperazin-1-ylmethyl)-2-phenyl-chromen-4-one (CH-f).

(1) Solubility and Log P

The solubility and log P of acetyl ChrysinMannich base derivatives see TABLE 1.

CH-j is pKa 5.3, log P 1.63 in Octanol/Water at 37° C. (about 2 times BA-j 0.69), solubility 2421 µg/ml in Octanol (about 6 times BA-j 377 µg/ml) and 56 µg/ml in water at 37° C. (BA-j 77m/ml). CH-j belongs to BCS II (low solubility, high permeability) and solubility presents the pH dependence. CH-j is solubility 574, 528, 78, 56 µg/ml, and dissolution 62%, 90%, <1.0%, <0.1%, at 37° C. in 0.1M HCl (pH1.2), 0.05M NaAC-HAC buffered solution (pH4.5), PBS (pH6.8) and water, respectively. CH-j is a pH dependent fast release. It is suggested that this product can be prepared by oral of solid dosage form. It is speculated that CH-j has more appropriate log P and solubility with more likely entering tissue cells than others solubility acetyl Chrysin Mannich base derivatives.

CH-f is pKa 4.9, log P 0.99 in Octanol/Water at 37° C., solubility 5511 µg/ml in Octanol at 37° C. (about 20 times BA-f 277 µg/ml) and 564 µg/ml in water at 37° C. (about 1000 times BA-f 0.53m/ml). CH-f is BCS I (high solubility and permeability) and solubility presents the pH dependence. It is speculated that CH-f has more appropriate log P and solubility with entering systemic (blood system and tissue cells) than others solubility acetyl Chrysin Mannich base derivatives.

TABLE 1

Solubility and log P of acetyl Chrysin Mannich base derivatives

| Mannich derivatives | Octanol µg/ml | H2O µg/ml | log P | Clog P | pKa | GibbsEnergy kj/mol |
|---|---|---|---|---|---|---|
| BA-j | 377 | 77.0 | 0.69 | 1.28 | 5.5 | −254 |
| CH-j | 2421 | 56.0 | 1.64 | 0.98 | 5.3 | −221 |
| is-CH-j | 3409 | 52.0 | 1.82 | 1.64 | 4.5 | −150 |
| CH-h | 2551 | 43.4 | 1.77 | 1.33 | 5.4 | −209 |
| CH-i | 733 | 6.2 | 2.07 | 0.79 | 4.8 | −82 |
| CH-d | 580 | 1.4 | 2.62 | 1.15 | 5.1 | −171 |
| CH-e | 120 | 0.1 | 3.08 | 1.87 | 4.8 | −45 |
| CH-f | 5511 | 564 | 0.99 | 1.30 | 4.9 | 46.5 |
| BA-f | 277 | 0.53 | 1.70 | 1.60 | 5.6 | −13.5 |

(2) Stability

According to the testing guidelines for drug stability test by FDA, raw material of acetyl Chrysin Mannich base derivatives is stable in the tests of high temperature, high humidity, and strong light exposure, accelerated and long-term stability. It is stable too in simulated artificial gastric juice, intravenous juice and intracellular juice.

(3) Influence of ROS Level in Cells

The cells are cancer cells (MCF-7, GBC-823, Hep G2) and normal cells (Liver, COS-7, PBMCs). According to the literature [Scientific Reports, 2015, 5: 13626; Anti-cancer Agents in Medicinal Chemistry, 2016, 16: 914-924.], in vitro cultured cells was given to CH-j 25 µM for 3.5 h, added PF1-$H_2O_2$ selective fluorescence probe 10 µM for 0.5 h and detected the concentration of $H_2O_2$ in cells, and performed fluorescence imaging by results shown in FIG. 1.

FIG. 1-1 Results showed that the effect of 4-hydroxypiperidine to improve the level of $H_2O_2$ by PF1-$H_2O_2$ selective fluorescent probe 10 µM in Hep G2 was most significant in acetyl Chrysin Mannich base derivatives. This is because of 4-hydroxypiperidine as a powerful antioxidant with capturing .$O_2^-$, releasing $H_2O_2$.

Figures 1, 2:
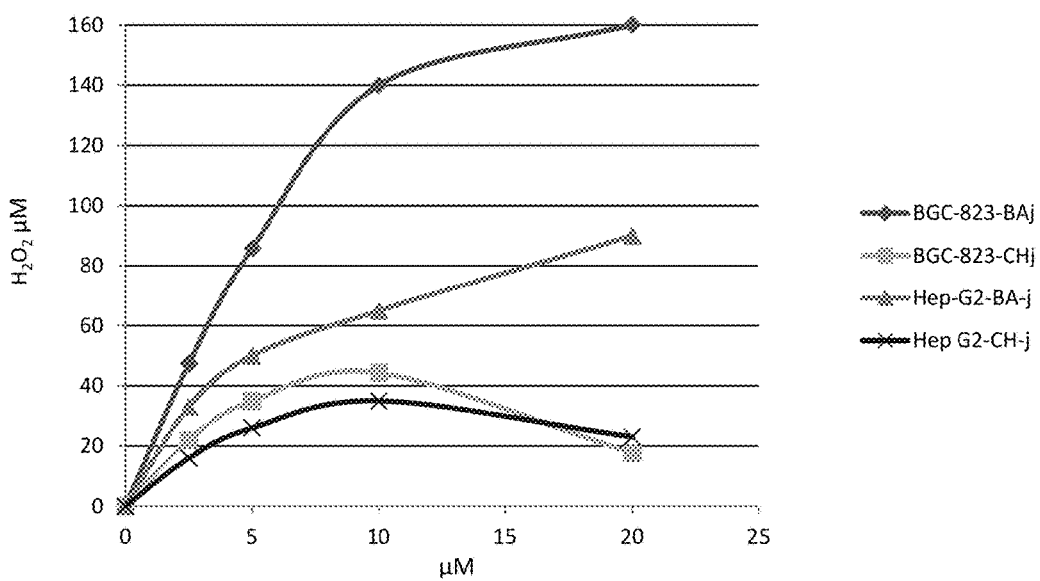
Figures 1, 2, 3:
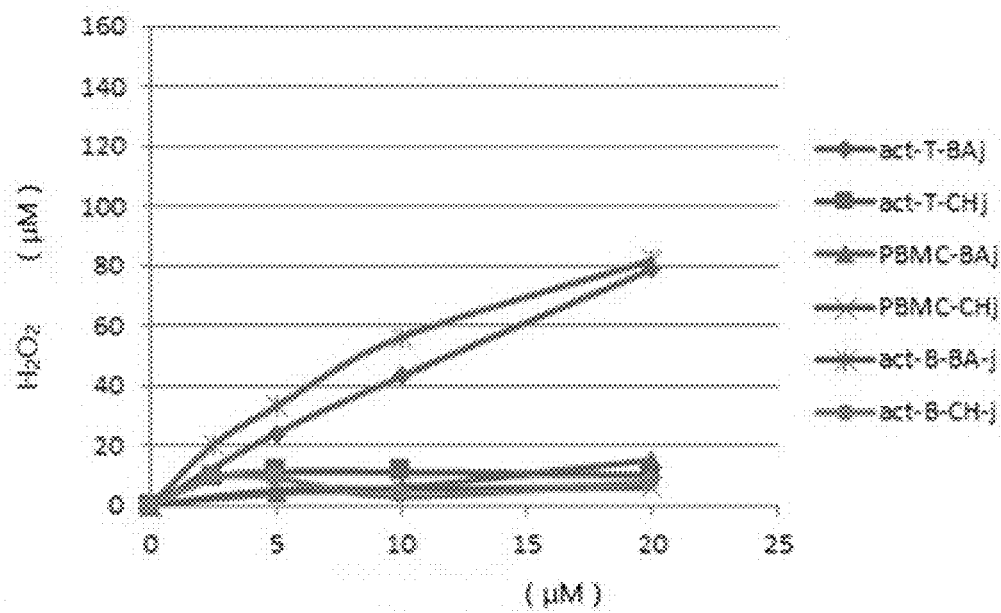
Figures 1, 2, 3, 4:
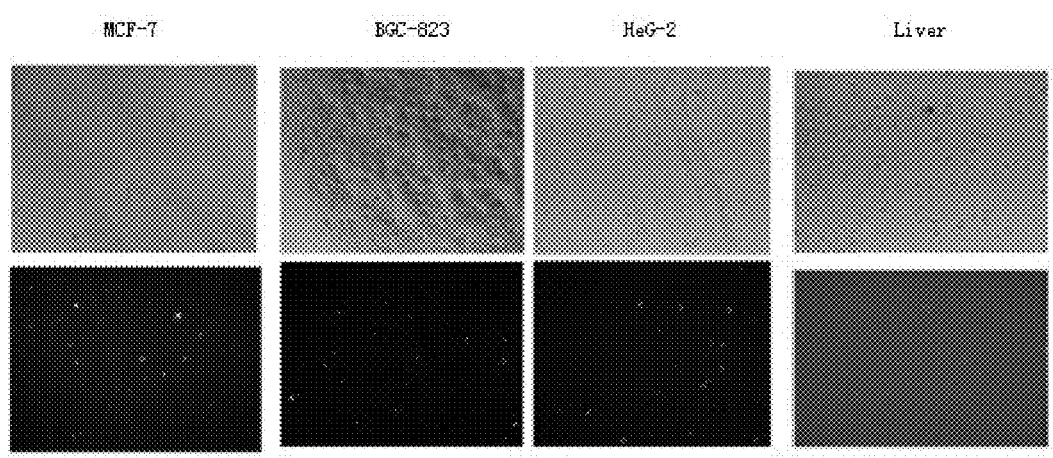

FIG. 1-2, 4, Results showed that the levels of $H_2O_2$ by PF1-$H_2O_2$ selective fluorescent probe 10 µM in BGC-823 and Hep G2 can be improved and present obvious dose-dependent manner in CH-j low dose range when the CH-j 5-10 µM, releasing about 4 times the amount of $H_2O_2$, maximum of 35-45 µM. But continue to improve the CH-j dose of $H_2O_2$ showed obvious concentration dose-dependent manner.

FIG. 1-3, FIG. 1-4, The fluorescence imaging by PF1-$H_2O_2$ 10 µM is that CH-j 12.5 µM for 4 h affected the level of $H_2O_2$ in MCF-7, GBC-823, Hep G2 and Liver. Results showed that the levels of $H_2O_2$ by PF1-$H_2O_2$ selective fluorescent probe 10 µM in PBMCs and activated lymphocytes were below 10 µM, CH-j no significant dose-dependent manner without obvious cell apoptosis and necrosis. The results indicated that the $H_2O_2$ level of 10 µM in PBMCs and activated lymphocytes by CH-j can was tolerable. (BA-j the levels of $H_2O_2$ in human normal Liver cells and PBMCs cells are below 10 µM, without apoptotic, necrotic and dose-dependent manner. However, the level of $H_2O_2$ in activated lymphocyte showed significant dose-dependent manner, with mass apoptosis and without necrosis.) The result indicated that the CH-j alternative to raise the $H_2O_2$ level of solid cancer cells and a little of PBMCs and activation of lymphocytes.

FIG. 1-5 Results showed that the levels of .OH$^-$ in HepG2 and LO2 were given by 12.5 µM of CH-j and CH-f for 5 h, than added CCy-OH selective fluorescent probe 5 µM for 0.5 h, than performed fluorescence imaging. [Sensors and Actuators B, 2016, 236: 60-66] The results showed that CH-j is present red fluorescence in MCF-7 and no in COS-7. This is because of the level of $Fe^{++}$ is 5-15 times in cancer cells than normal cells, CH-j is capturing .$O_2^-$ and releasing higher levels of $H_2O_2$, than into ($H_2O_2$/$Fe^{++}$)=.OH$^-$. [Life Sciences 2006, 4] The results indicated that CH-j can release .OH$^-$ in cancer cells and no in normal cells.

FIG. 1-6 Results showed that MCF-7 and COS-7 was given by Rh—NO selective fluorescent probe 5 µM for 0.5 h, than added 25 µM of CH-j and CH-f for 12, 24, 48 h, than performed fluorescence imaging. [Organic Letters, 2008, 10: 2357-2360] The results showed that CH-f is present stronger red fluorescence than CH-j in MCF-7, and without COS-7. The results indicated that CH-f is better releasing NO than CH-j in cancer cells and without in normal cells. This is because of cycloalkylamine-methyl releasing NO by Cope reaction, and the higher level of NO 4-methylpiperazine than 4-hydroxypiperidine.

In vitro cultured Hep G2 was given by BODTPY-OCl selective fluorescent probe 5 µM for 0.5 h, added CH-j 40 µM or HCPT 5 µM for 4 h, and performed fluorescence imaging. The results showed that CH-j was not present yellow green fluorescence in Hep G2 without in normal liver cells, but present fluorescence HCPT in control cells. The results indicated that CH-j can inhabitant production NaOCl in solid cancer cells but HCPT can improve the level of NaOCl.

The result demonstrates that CH-j alternative to raise the $H_2O_2$, —OH$^-$ and NO level of solid cancer cells with little of PBMCs and activation of lymphocytes. This is because of CH-j log P is large, and plasma protein binding force weak, thus relatively it is stronger binding with solid cells but weaker with PBMCs and activated lymphocytes. Therefore, suggested that CH-j is more suitable for solid tumor. (BA-j log P is small and plasma protein binding force large, thus relatively it is weaker binding with solid cells but stronger with activated lymphocytes. So, BA-j is more suitable for the blood system.)

(4) Antiproliferation Activity of Cancer Cells

The results of antiproliferation activity of BGC-823 in vitro showed in FIG. 2. The results showed that Mannich base derivatives of acetyl Chrysin were significant dose-dependent manner in the range of 1.25-20 μM, and the anti-proliferation activity intensity of the derivatives similar without significant difference.

Anti-cancer cells proliferationactivity of in vitro CH-j and CH-f were shown in TABLE 2 for the results of the screening of 5 cancers cells. The anti-proliferative activity intensity of CH-j and CH-f $IC_{50}$ are 6.3 μM (2.6 μg/ml) and 5.6 μM (2.3 μg/ml) with 5 times stronger than Chrysin ($IC_{50}$ 30 μM, and 2 times stronger than BA-j ($IC_{50}$ 12.3 μM, 4.7 μg/ml). (According to FDA "anti-cancer drug pharmacodynamics guidelines" regulation, when synthetic compounds or plant extraction and refinement of $IC_{50}$<10 μg/ml or plant crude extracting $IC_{50}$<20 μg/ml, as has antitumor activity in vitro.) These results indicated that the introduction of the acetyl to improve anticancer activity plays a key role.

TABLE 2

Anti-cancer cells proliferationactivity of CH-j and CH-f (MTT, 48 h)

| $IC_{50}$ μM | BA-j | CH-j | CH-f |
|---|---|---|---|
| MCF-7 | 10.6 ± 0.30 | 5.7 ± 1.24 | 5.2 ± 1.24 |
| H-460 | 13.7 ± 1.83 | 6.5 ± 1.13 | 5.6 ± 1.33 |
| BGC-823 | 12.3 ± 1.73 | 6.3 ± 1.13 | 5.2 ± 1.21 |
| PC-3 | 12.8 ± 2.06 | 6.2 ± 1.16 | 5.1 ± 1.17 |
| Hep G2 | 15.7 ± 1.30 | 6.0 ± 1.50 | 6.1 ± 1.45 |
| AV | 12.3 | 6.3 | 5.6 |

(5) Induce Apoptosis of Cancer Cells

Hoechst 33258 is an active fluorescent dye with DNA specific binding, which is mainly combined with base area of DNA, which emits blue fluorescence when stimulated by ultraviolet light. The living cells emit uniform fluorescence, the apoptotic cells are bright blue fluorescence due to their chromatin fixation, dense and concentrated nuclei.

MCF-7 was treated with 0, 5, 10, 20 μM of CH-f and CH-j for 24 h, Hoechst 33258 fluorescence staining, and cell morphological changes were shown in FIG. 3-1. With the increase of drug concentration, cell count decreased significantly, and the nucleus from compact fluorescent, nuclear membrane of the edge of the visible apoptotic body apoptotic cells, apoptosis cell percentage in dose dependent increase. CH-f and CH-j are completely different from the cytotoxic drug HCPT, which appears to be apoptotic at low doses and necrotic at high doses in BGC-823. These results indicated that CH-f and CH-j were induce apoptosis of BGC-823 and without necrotic.

PI specificity is combined with DNA, and the fluorescence intensity is in a good linear relationship with the combination of PI. After cell fixation, PI staining was used for quantitative analysis of DNA content in cells by flow cytometry. Since the amount of DNA in different cell cycles varies, it can be determined that the drug actions on the cell cycle. In cell apoptosis, there are many characteristic changes in the cell and molecular level, and the most characteristic of the change of nucleus is the change of nucleus. Due to activate apoptosis cells, DNA degradation, reduce the cell DNA, and therefore can be in the G0/G1 peak appeared before a diploid apoptosis peak (sub-G1), 185 Da pyrolysis peak integer times of DNA, no less than 185 Da pyrolysis peak.

BGC-823 was treated with CH-j for 24 h, and the results of PI fluorescence staining were shown in FIG. 3-2. CH-j can be used to block the BGC-823 in G1, G2 phase, and increase the proportion of apoptosis to dose dependent growth. In addition, high concentrations of drugs can also reduce the proportion of S stage cells. The results showed that CH-j was enough to prevent the cancer cell cycle from G1 and G2/M, and decrease the number of cells in S phase. These results indicated that CH-j induced significantly apoptosis of BGC-823.

There is a series of morphological characteristic changes in the apoptosis of cells, in which the change of the plasma membrane is one of the characteristics of early apoptosis. The cytoplasm is flipped from the inside of the cytoplasm to the outer surface of the cell when the cell apoptosis, Annexin V is a $Ca^{++}$ dependent phospholipid binding protein, which has a high affinity with phospholipid-peptide-serine, which can be combined with the phospholipid peptide specificity that is exposed to the extracellular cells. However, cytoplasm transfer to cell membrane is not unique to apoptosis, but also can occur in cell necrosis. The difference between the two cell death modes is that the cell membrane is intact in the initial stage of apoptosis, and the integrity of the cell membrane in its early stage is destroyed. PI is a nucleic acid dye that cannot pass through the intact cell membrane, but in the cell and necrotic cells in the middle and late stage of apoptosis, the PI can dye the nucleus through the cell membrane. Annexin V-FITC-PI was used to detect apoptosis and necrotic cell ratio on flow cytometry.

BGC-823 was treated with CH-j for 24 h, and the results of Annexin V-FITC-PI double fluorescence were shown in FIG. 3-3. CH-j can induce apoptosis the BGC-823 with obvious dose-dependent manner, little early necrotic cells, the proportion of early apoptosis cells and the proportion of late apoptotic cells increased significantly. Thus, the early apoptotic cells increased significantly with the increase of drug concentration. A relatively small increase in apoptotic cells is increased. HCPT can induce apoptosis at low doses, and high dose can cause the inflammatory necrosis of early cells. These results indicated that the anti-proliferation activity of CH-j without cytotoxic drugs was mainly achieved by inducing the apoptosis of BGC-823, and without directly killing cells caused the inflammatory necrosis of the cells.

Caspase is a series of cysteinyl aspartate specific proteinase in the cytoplasm of protease with closely related to cell apoptosis, and participate in cell growth, differentiation and apoptosis regulation. Caspase is same key enzymes in apoptosis process and in the apoptosis of the mediated cells, there are almost all apoptotic signaling pathways involved in the pathway of caspase. Caspase active site for cysteine-SH, exists in the inactive state of pro-caspase, it is more sensitive to $H_2O_2$, when the $H_2O_2$ oxidation-S—S-dimer form, was activated into caspase-S—S-caspase, enlarge activity by continuous activation induced apoptosis. Caspase-8 is an early starter for the induction of apoptosis, and the caspase-3 is the late executor. Pro-caspase-9 is dissociation with phosphorylation surviving, and inhibiting cell apoptosis and promoting division. Pro-caspase-9 by $H_2O_2$ is oxidized into caspase-9-S—S-caspase-9 with inhibiting cell division and inducing apoptosis. $H_2O_2$ can directly oxidize and activate caspase, hydrolyze antiapoptotic protein Bcl-2 and Bcl-xl substrate, so selectively induce apoptosis of cancer cells and reduce the damage of normal cells.

BGC-823 was treated with CH-j for 24 h, test results of caspase-3, 8, 9 were shown in FIG. 3-4-C. In the range of 0-10 μM, CH-j activated caspase-3, 8, 9 both in a dose-dependent upward trend, and the increase of CH-j dose activity no longer showed an upward trend. These results indicated that CH-j selective induction of cancers apoptosis was related to the activation of $H_2O_2$ oxidative activation of caspase-3, 8, 9.

Besides, MCF-7 was treated with 50 μM of CH-f and CH-j for 9 h and 24 h can cause autophagy without BA-j. And MCF-7 was treated with 10 μM of CH-f and CH-j for 24 h Bcl-2 expression can be suppressed similar to 20 μM of BA-j.

(6) Influence of HIF-1

The main site of HIF-1α inhibition is on Cys-SH oxidized by $H_2O_2$ and $.OH^-$, on $P^{402}$ and $P^{564}$ Pro-NH are hydroxylated by proline hydroxylase (PHD), or by oh-oxidation. $K^{532}$ and $T^{796}$ are phosphorylated. $K^{532}$ is acetylation. HIF-1α is located on $C^{800}$Cys-SH, the first active site, and the second irreversible activity site at on $P^{402}$ and $P^{564}$ proline amino (pro=NH).

In low oxygen state, PHD inactivation, rich cysteine-SH on (p300-sh/CBP) has the activity of HIF-1α. In the normal oxygen state, the PHD would deactivate the HIF-1α on $P^{402}$ and $P^{564}$ hydroxyl hydroxyl into pro-NOH. PHD can remove the immune suppression of T cells, inhibits the metastasis of cancer cells. [Cell, 2016, 166: 1117-1131.] HIF-1α $C^{800}$Cys-SH is sensitive to $H_2O_2$, and $H_2O_2$ has been oxidized to Cys-S—S— without temporarily active. Under hypoxia, Cys-S—S— can be reduced into active Cys-SH by p300-SH. $H_2O_2/Fe^{2+}$ formed hydroxyl radical $(.OH^-)$ in the high level $H_2O_2$ state, turning the pro-NH into pro-NOH, Cys-S—S— oxidation as $Cys-SO_2H$, and the formation of HON=HIF-1α-$SO_2H$ rapidly degradation by the ubiquitin-protease pathway. HIF-1β without cysteine-SH as the active switch, so it is not affected by $H_2O_2$ and $.OH^-$.

BGC-823 was treated with 0, 2.5, 5, 10 μM CH-j for 1 h, then the 2 μM insulin was added, and 2 h were cultured, and the cells were collected and lysed. HIF-1α and HIF-1β were determined by immune-printing method, and the results of HIF-1β were shown in FIG. 4. The results showed that CH-j inhibited HIF-1α expression in a dose-dependent manner, without affecting the expression of HIF-1β. These results indicated that CH-j is a HIF-1α selective inhibitor with selectively inducing apoptosis of solid tumor cells and inhibiting metastasis.

(7) Special Safety

According to FDA drug special security experiment research guidelines, 0.2% CH-j glucose injection, according to the excitant, allergic special safety evaluation method and the hemolytic test, besides have fever on cornea excitant, other are all negative. These results indicated that CH-j meets the requirements of injection or external use.

(8) Protein Binding Rate and Reversible Binding Rate

The combination of drugs and plasma proteins is usually reversible, and the affinity strength is determined by the reversible binding rate of the drug-protein complex. Only free drugs can spread to the tissue through the lipid membrane. By modifying the structure of the drug, the effect of the drug on the target site can be improved by improving the reversible binding rate of the drug-protein complex.

TABLE 3

Protein binding rate and reversible binding rate of CH-j

| Drug concentration | Protein binding rate % | | Reversie binding rate % | |
| --- | --- | --- | --- | --- |
| μg/ml | BA-j % | CH-j % | BA-j % | CH-j % |
| 50 | 89.6 | 84.9 | 20.2 | 90.1 |
| 25 | 92.5 | 84.4 | 21.0 | 89.6 |
| 12.5 | 93.3 | 88.6 | 19.1 | 90.3 |
| AV | 91.8 | 86.0 | 20.1 | 90.0 |
| SD | 1.9 | 2.2 | 1.9 | 0.5 |

The acidic part of polyphenol hydroxyl group is combined with lysine alkaline site in albumin structure. The protein binding rate and reversible binding rate of CH-j see TABLE 2. The 6-acetyl group weakened the affinity of the acidic part with the white protein alkaline site, so that the reversible binding rate of the CH-j protein complex was significantly greater than that of BA-j. These results indicated that the permeability of CH-j was good in both internal and extern, and mainly distribution in the whole body. Therefore, CH-j is easier to enter tissue cells and will be more effective on solid cancers than BA-j. (BA-j is mainly distributed in the blood, which is more effective for blood system cancer and immune system.)

(9) Pharmacokinetic

Chromatographic conditions and the system applies: with $C_{18}$ chromatographic column (acid the tall secretory effect, 5 μm, 4.6*150 mm), in acetonitrile-methanol-water-mesylate (25:20:55:0.15) as mobile phase, detection UV 283 nm, the velocity 1 ml/min, and the sample volume 20 μl. The theoretical plate number is not less than 2000 according to CH-j peak.

Sample solution: after the macaques were drugged, the catheter was inserted. The urine by oral CH-j 5 mg/kg is collected, added the methanol at 1:4 (v:v), centrifuge and remove the liquid to measure. Control solution is CH-j methanol solution 5 μg/ml. The results showed that the concentration of urine drug concentration-time curve in monkey (5 mg/kg) was shown in FIG. 5. The log P of CH-j is larger, the fat solubility strong, and absorption distribution in the body very rapid, the urine drug concentration-time curve consistent with the typical two-compartment model. Tmax1, 1.3 h, Cmax1 is 26.4 Mm. The redistributive period Tmax2, 9 h, Cmax2 is 13.2 μM (>$IC_{50}$ 6.1 μM). CH-j concentration in the urine slowly decreased with time, and 24 h was less than 3 μM. To eliminate phase half-life $t_{1/2\ \beta}$ is 6.2 h. The apparent distribution volume (Vd) 42 L, mainly distributed in body fluid (BA-j Vd 12.6 L, mainly distributed in blood. See Fitoterapia, 2015, 107: 36-34)

The comparison results of the pharmacokinetic parameters of the rhesus in monkey and the BA-j were shown in TABLE 5. The maximum drug concentration in CH-j (26.4 μM) was about 40 times higher than that of Chrysin (0.64 μM). These results indicated that CH-j was more readily distributed in tissue cells than BA-j, and presumably more effective for solid cancers.

TABLE 4

Pharmacokinetic parameters of CH-j by oral in monkey (n = 6)

| Drugs | CH-j | BA-j |
| --- | --- | --- |
| p.o. (mg/kg) | 3 | 3 |
| T max (h) | 1.3, 9 | 2.0 |
| $t_{1/2\beta}$ (h) | 6.2 | 4.2 |
| C max (μM) | 26.4 | 25.4 |
| AUC 0-∞ (μM · h) | 20.4 | 71.5 |
| V d (L) | 42.0 | 12.6 |

(10) Main Metabolic Pathways of CH-j (I) Neutral degradation in normal cells: CH-j is hydrolyzing into Hydroxy-phenyl-acetic acid (M152), 1-(2, 4, 6-Trihydroxy-phenyl)-ethanone (M168) and N-hydroxymethyl-piperidin-4-one (M129) as the main metabolic pathways.

(II) Acid degradation in liver: Secondly CH-j is hydrolyzing into metabolite Sulfuric acid mono-[1-(2, 4, 6-trihydroxy-3-methyl-phenyl)-ethyl] ester (M264) and Benzoic acid with combining Glycine amino acid into Hippuric acid (M179).

(III) Alkaline degradation in blood: Slight CH-j is hydrolyzing into 2-Methyl-3-aza-bicyclo [3.3.1] nona-1(8), 2, 5(9), 6-tetraene-6, 8, 9-triol (M179) and Hydroxy-phenyl-acetic acid (M152).

of $.O_2^-$, releasing slight of $H_2O_2$, and degrading into N-hydroxymethyl-piperidin-4-one (M129) without continually degrading.

Due to lots of $.O_2^-$ and $Fe^{++}$ in cancer cells, CH-j is capturing $.O_2^-$, releasing higher level of $H_2O_2$ and $.OH^-$, producing Baicalein (M270) by Darkin oxidation with further degrading into 2, 3-Dioxo-3-phenyl-propionic acid (M178), and N-Hydroxymethyl-piperidin-4-ol (M131) with further degrading into 5-Hydroxy-pent-1-en-3-one (M100) and NO by Cope elimination reaction.

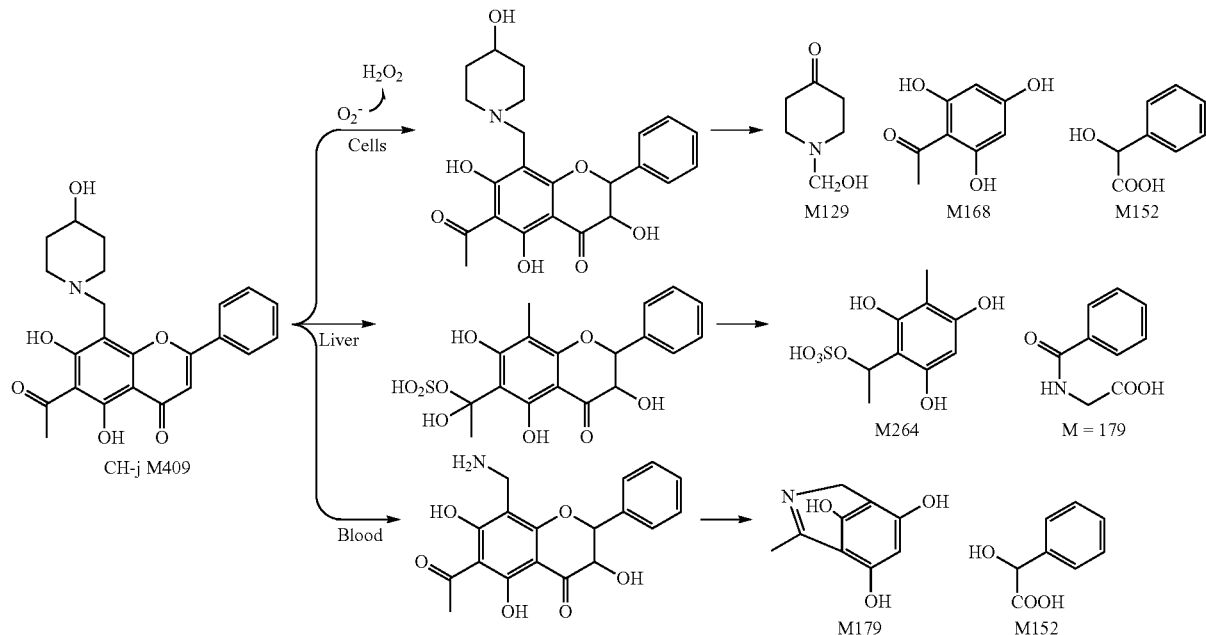

The small molecule metabolites were excreted in urine. Due to a bit of $.O_2^-$ in normal cells, CH-j is capturing slight

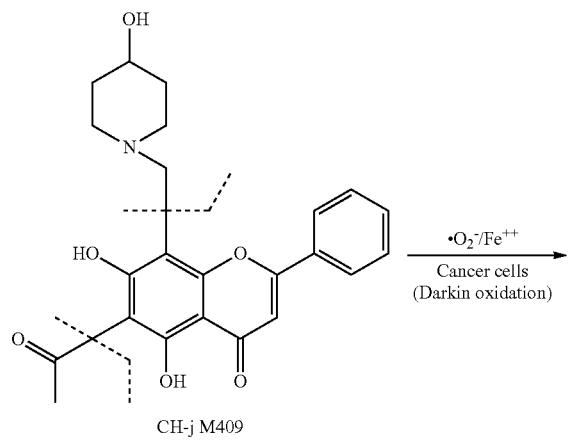

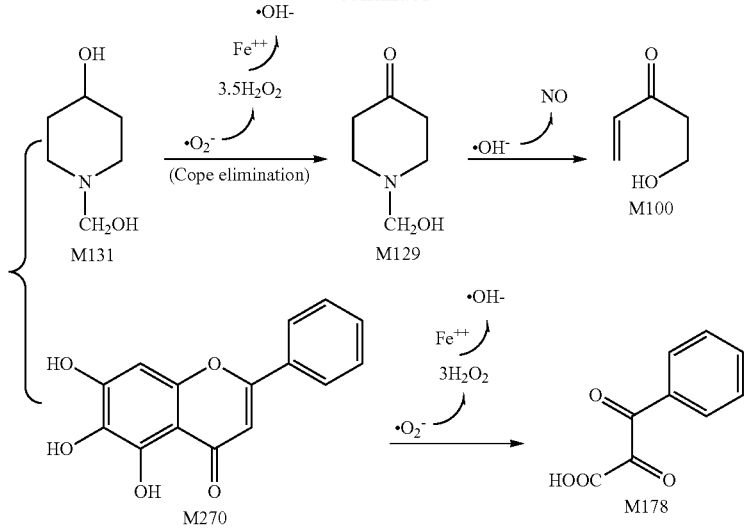

Due to the poor solubility and the strong "liver first pass effect" of glucose aldehyde acid metabolism (>95%) and "hepatoenteral circulation", bioavailability of Chrysin is very low. Flavopiridol, p276-00 and Vorciclib of Chrysin-organic amine derivatives, duo to mainly C7-glucose aldehyde acidification metabolites by oral, only a small amount is into the tissue cells. In the tissue cells, it is not easy to be metabolized in part because of the organic amine substituents, thus producing strong cytotoxicity. Due to format the stable six-member ring structure by intermolecular hydrogen of CH-j bonds between phenolic hydroxyl and acetyl or Mannich amine, the "liver firs effect" of glucose aldehyde acidification metabolism (M585<1%) and "hepatoenteral circulation" can be effective inhibited with improving bioavailability significantly. CH-j can enhance I phase metabolism and inhibit II phase metabolism. The metabolic pathway of CH-j is independent of CYP3A4. [Scientific Reports, 2015, 5: 13626; Fitoterapia, 2015, 107:36-34.]

(11) Organization Distribution

Figures 1, 2, 3, 4, 5:
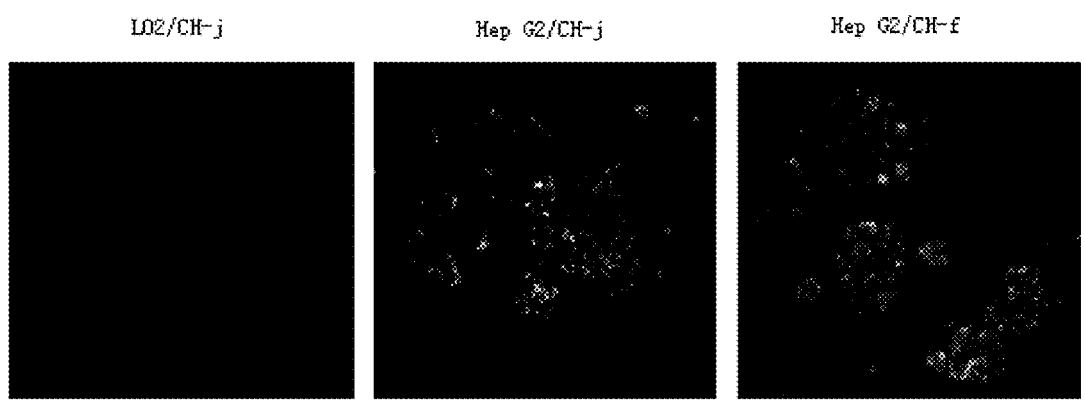
Figures 1, 2, 3, 4, 5, 6:
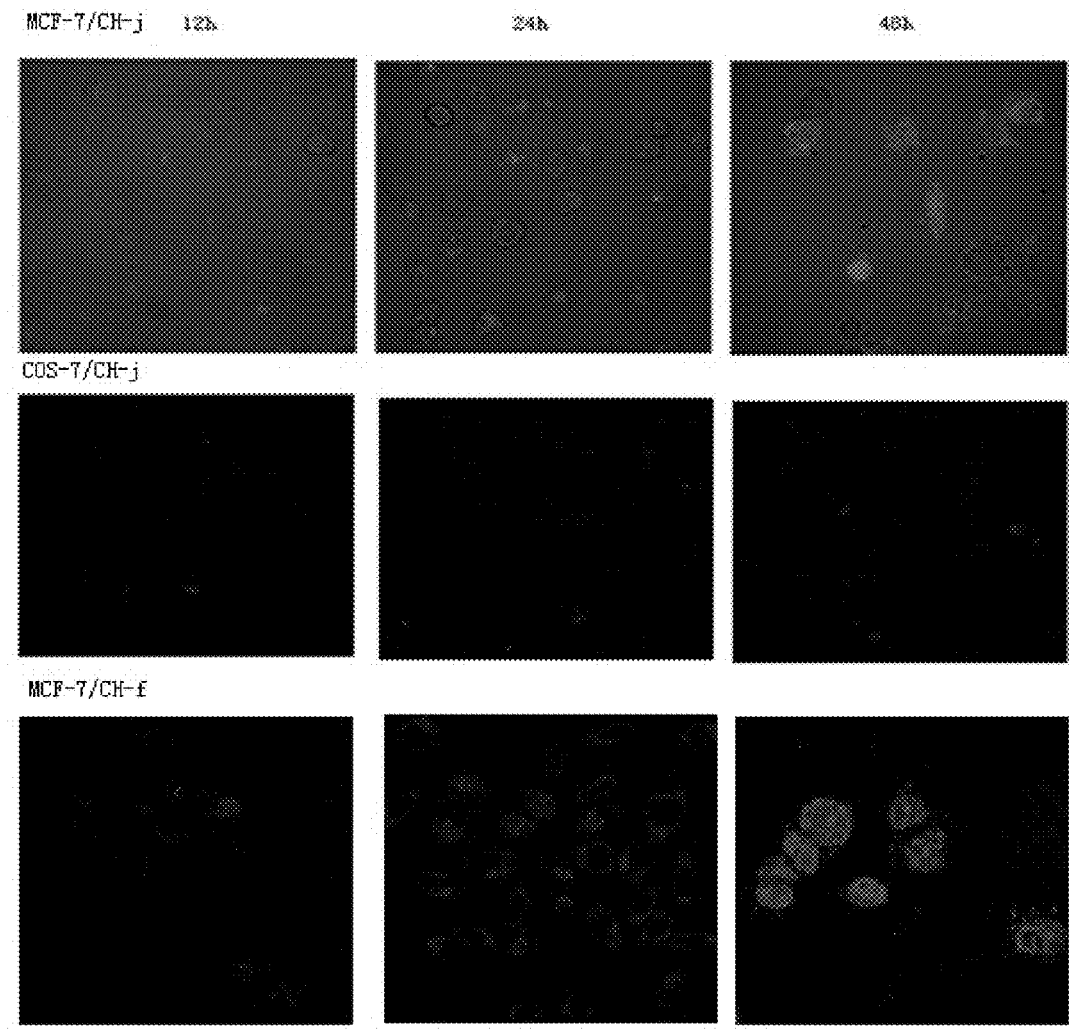
Figure 2:
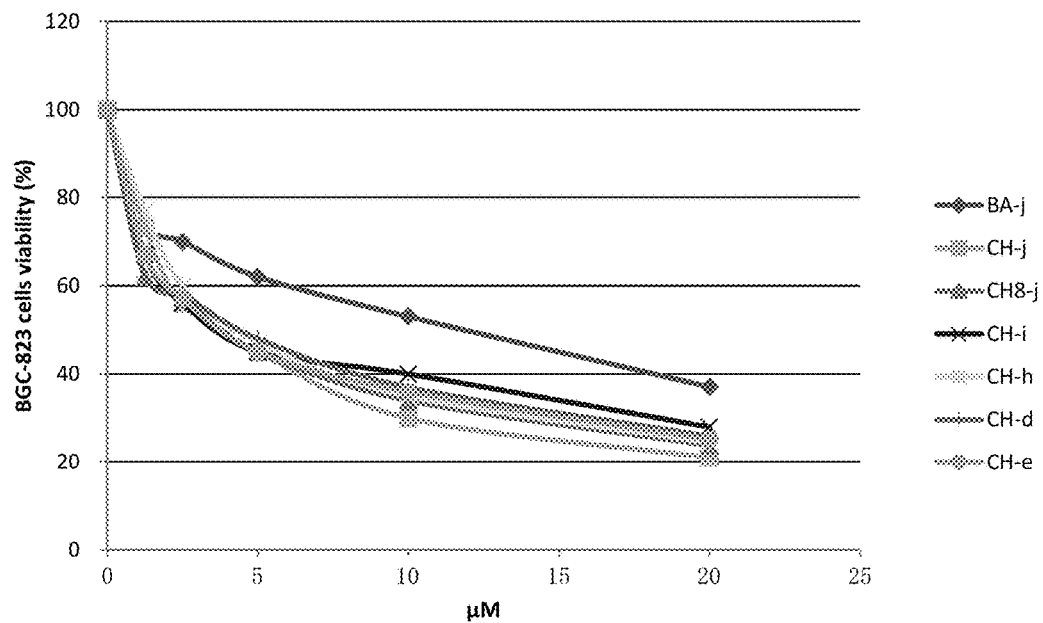
Figures 1, 3:
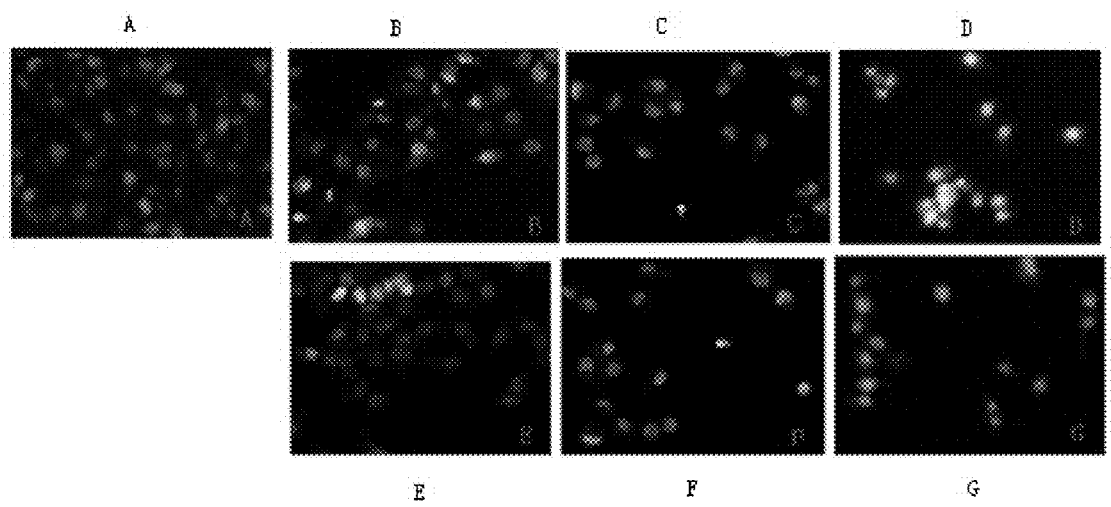
Figures 2, 3:
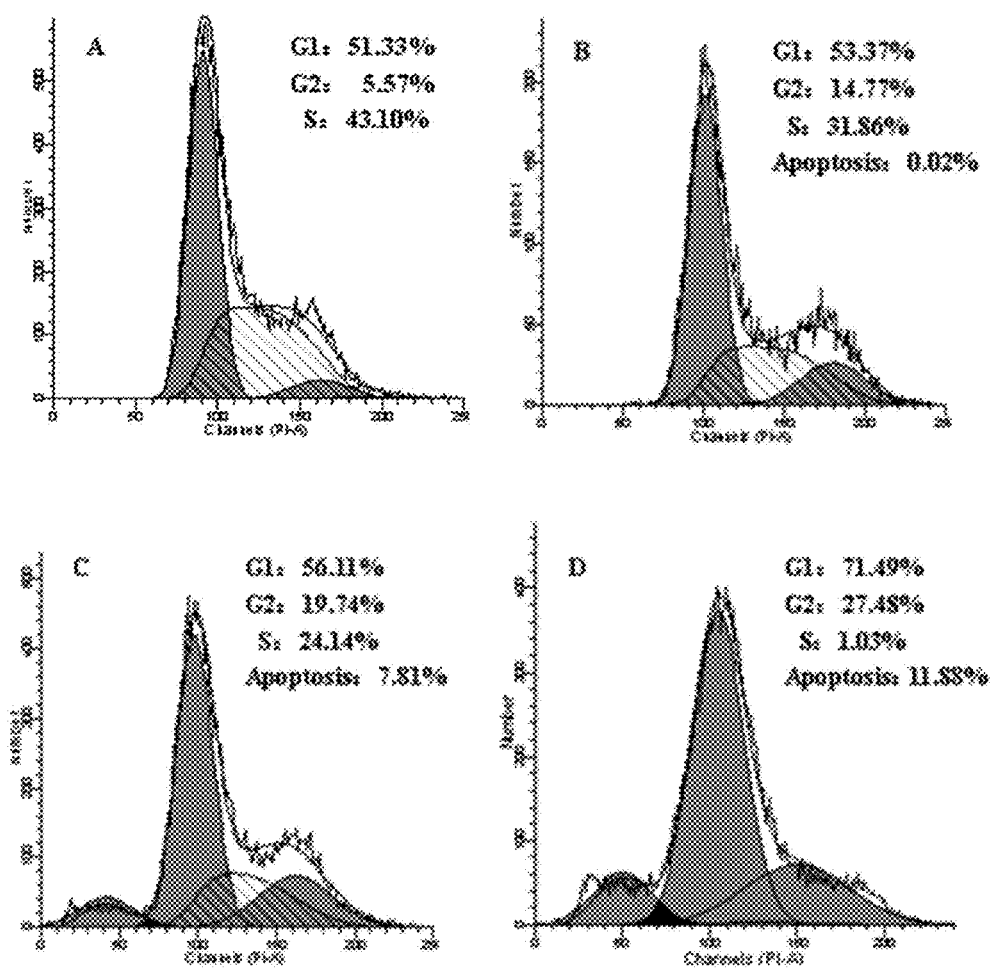
Figure 3:
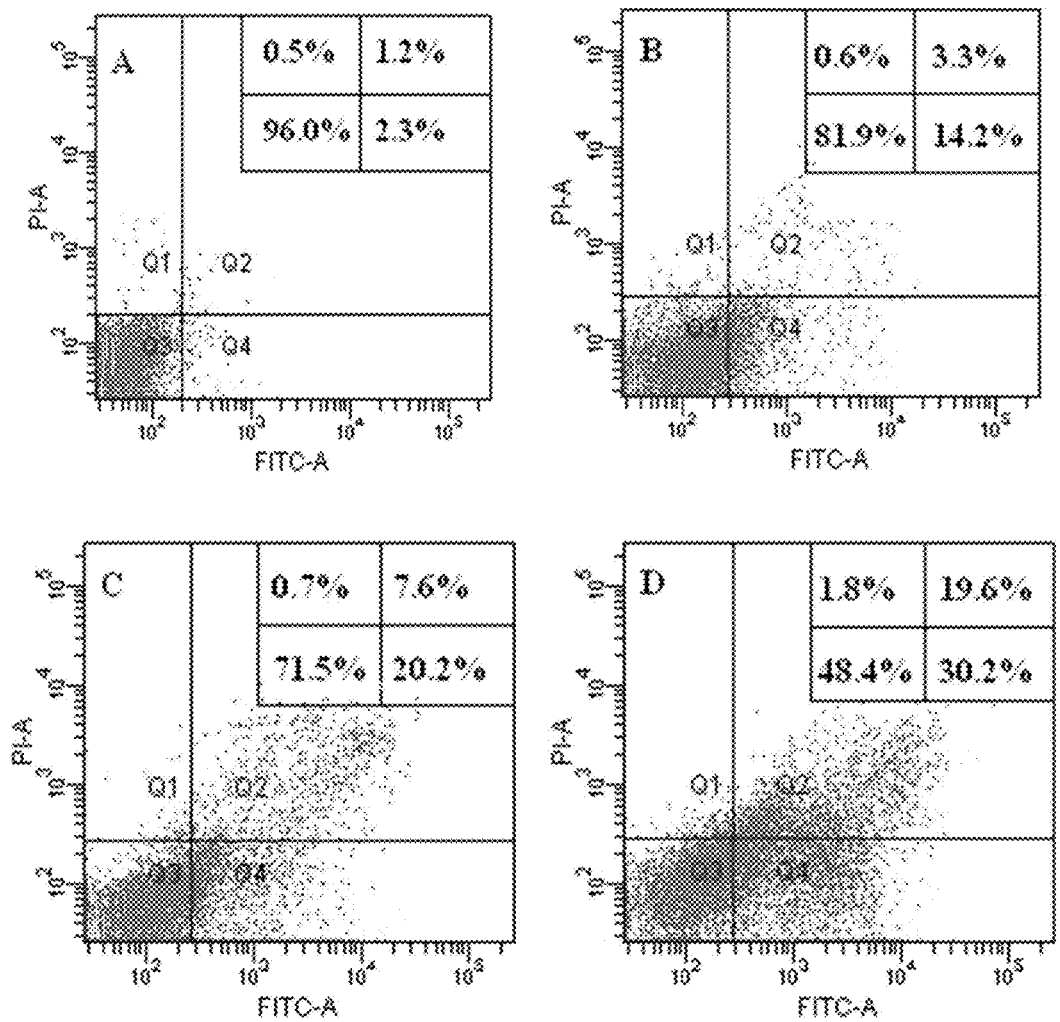
Figures 3, 4:
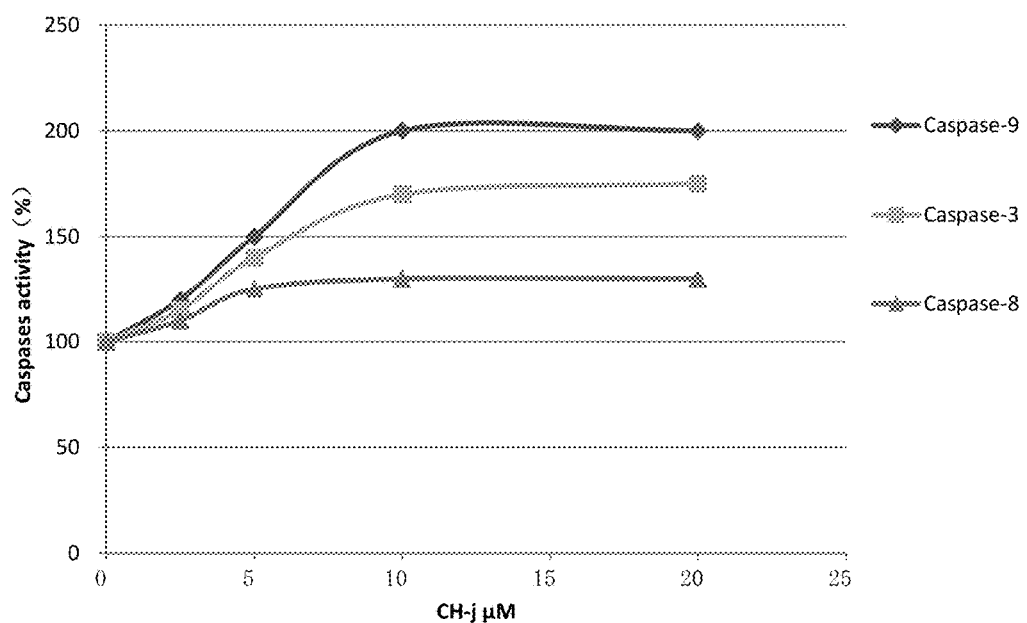
Figure 4:
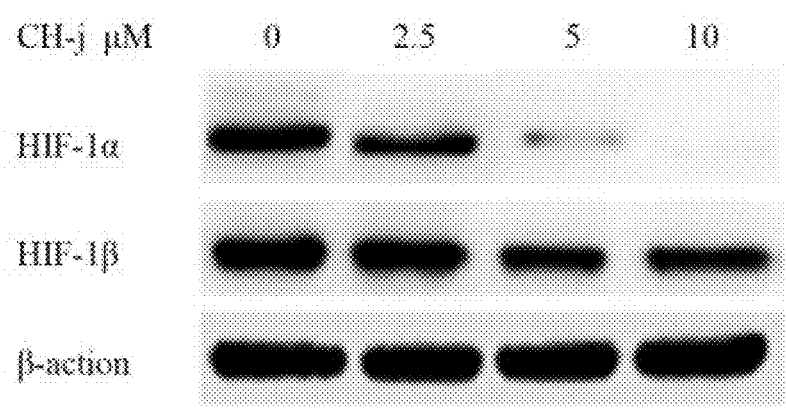
Figure 5:
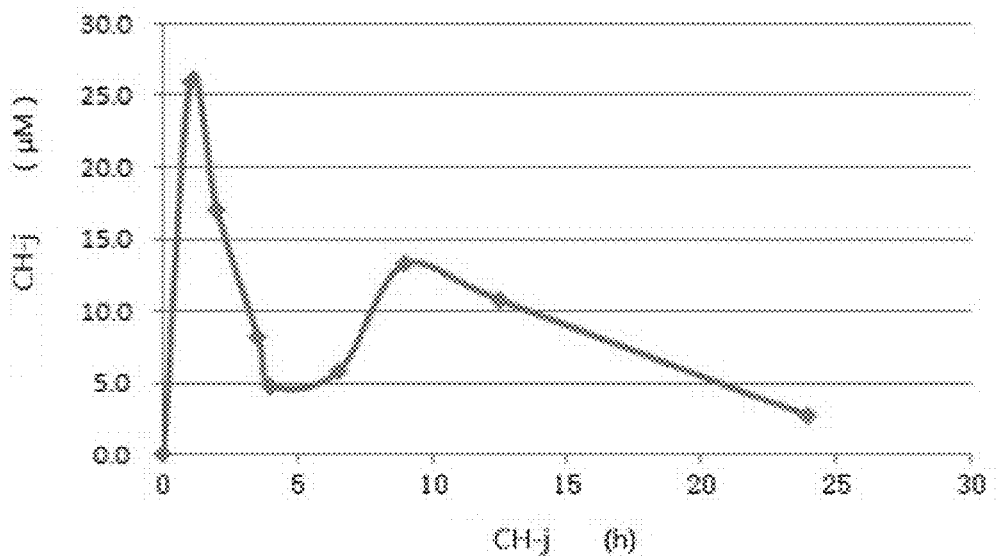
Figure 6:
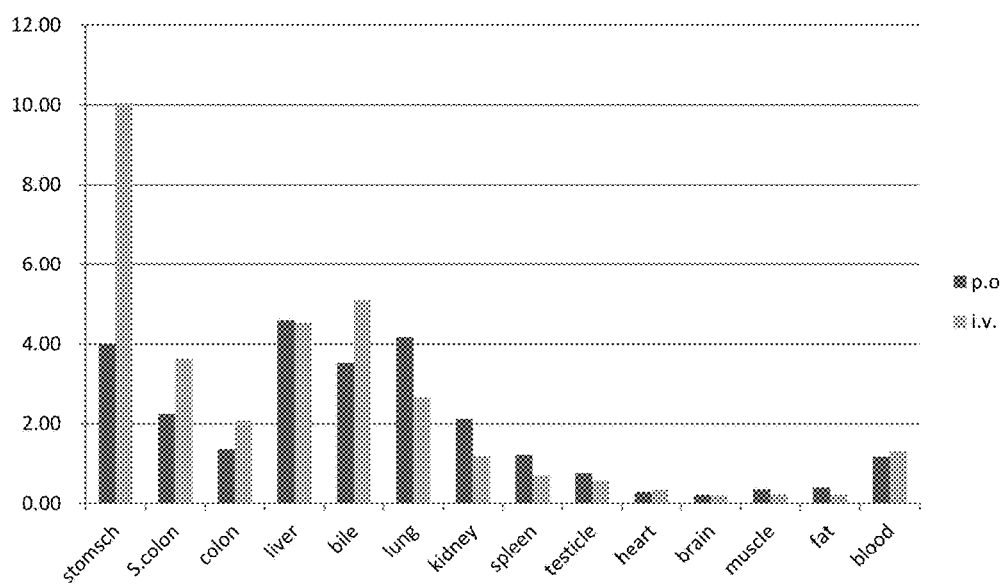

The distribution results of CH-j tissue distribution were shown in FIG. 6, when CH-j 100 mg/kg rat by venous intravenous (i.v.) or oral (p.o.) 2 h. In the blood, urine, bile and tissues, the prototype drugs and metabolites can be detected. CH-j by oral in the stomach concentration of the large, about 2 time higher than other tissues. It showed that the CH-j was mainly absorbed in the stomach and had a high drug concentration, which had no special affinity for all tissues and was able to pass the blood-brain barrier. Compared with the intravenous administration, the oral administration was completely absorbed and the bioavailability was close to 100%.

Drug into the blood system, due to CH-j large log P, plasma protein binding is moderate, strong permeability, prototype drug quickly into the tissue cells, and to be abnormal activation of lymphocytes in the blood almost no affinity.

In contrast, the BA-j can detect the prototype drugs only in blood and urine, but the prototype drug can not be detected in the tissues, only the metabolite M179 can be detected. Show mainly in the gastrointestinal tract absorption, through the liver portal vein absorption into the blood circulation, due to BA-j the log P is small, plasma protein conjugation rate is too high, the binding force is too strong, mainly distributed in the blood system prototype drugs, to have a special affinity is abnormal activation of lymphocytes, rarely into the tissue cells except absorption parts.

(12) Anti-Tumor Activity in the Body

Figure 7:
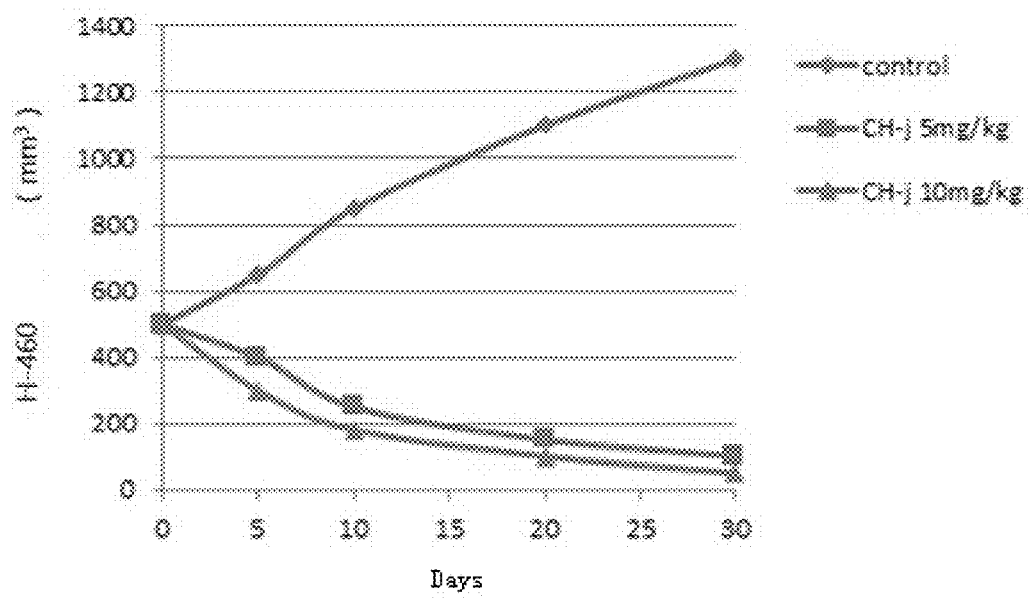

The anti-tumor effect of the BALB/c nude mouse model of the non-small cell lung cancer (H-460) was determined by the method [Scientific Reports, 2015, 5: 13626], and the results were shown in FIG. 7. 5 or 10 mg/kg of CH-j, for twice daily 10 days were compared with the control group. CH-j can significantly inhibit the growth of the H-460 xenograft in the body. Compared with before, the reduction rate of H-460 tumor was 90.5%±9.2% and 95.2%±11.6% ($P<0.05$), respectively. The results indicated that CH-j inhibits the growth of H-460 xenograft in vivo by reducing significantly tumor size.

(13) CDK1 Selective Inhibition Activity

The acetyl Chrysin Mannich base derivatives belongs to CDK1 selective inhibitor, the results that inhibiting CDK1 $CC_{50}$ of CH-j and CH-f were 0.15 μM and 0.13 μM (about 2 times stronger than $CC_{50}$ of BA-j 0.3 μM)) by according to the literature [Scientific Reports, 2015, 5: 13626].

(14) Action Mechanism

It is necessary that solid cancers cell survival under hypoxic conditions must rely hypoxia inducible transcription factor (HIF-1a). HIF-1α is closely with cell proliferation, angiogenesis, invasion and metastasis, such as apoptosis and drug resistance. The University of California and Stanford University suggested that HIF-1α will be the most effective target for the treatment of solid cancers, and has become the hotspot of current research on anti-cancer drugs. [Nature, 2015, 524: 298-300; Cell, 2015, 163: 1288-1288.e1; Nature Reviews Cancer, 2012, 12: 9-22; Nature Reviews Cancer, 2003, 3: 721-732; Nature Medicine, 2003, 9: 667-84: Nature Reviews Drug Discovery, 2003, 2: 1-13]

The body uses oxygen to produce energy. But if oxygen levels drop, cells into anoxic condition, no longer generate energy, but the conversion of $.O_2^-$, activation of HIF-1α to close the $H_2O_2$ generated, and sends a signal to the inflammatory cells to let their migration to the anoxic area. [Cell, 2015163:1288-1288.]

In normal cells $.O_2^-$ can be captured by SOD and released $H_2O_2$, which forms the first natural defense of the body. Excessive $H_2O_2$ is mainly mediated by GPX catalyzing the oxidation of the reduced GSH to GSH. Some $H_2O_2$ has been mediated by CAT for $H_2O$ and $O_2$. Therefore, $.O_2^-$ and $H_2O_2$ are maintained at a very low level by SOD and GPX control, making the cells non-proliferative.

The level of $.O_2^-$ is the higher in cancer cells than normal cells, and $H_2O_2$, SOD, GPX and CAT are lower than normal cells. [European Journal of Pharmacology, 2010, 630:121-130.] The proliferation and metastasis of cancer cells requires a lot of oxygen consumption, so hypoxia is an important feature of the microenvironment of solid tumor. The survival of cancer cells in low oxygen state depends on HIF-1α, HIF-1α accumulation to promote expression of growth factors such as VEGF. VEGF plays a crucial role in cancer angiogenesis, which is essential for the growth and metastasis of cancer. Therefore, the anti-HIF-1/VEGF angiogenesis therapy system is a promising strategy for treating cancer. [Molecular Cancer Therapeutics, 2007, 6:220-226.] The Cancer cell HIF-1α was expressed in low oxygen state, causing the cell to be in a proliferating state, and the sensitivity of $H_2O_2$ was increased. Therefore, with the same concentration of $H_2O_2$, cancer cells are more likely to apoptosis than normal cells. The high levels of $H_2O_2$ can specific target oxidize enzymes with cysteine as the active site (as CDC25, HIF-1α, caspase), activate intracellular apoptosis pathway without extrinsic death receptor pathway, thus selectively induce apoptosis in solid tumor cells.

Base on the levels of $.O_2^-$ and $Fe^{++}$ are higher 5-15 times in cancer cells than in normal cells, CH-j is capturing $.O_2^-$ and releasing higher levels of $H_2O_2$, than into $.OH^-$ ($H_2O_2$/ $Fe^{++}$) with most critical ROS for degrading DNA in cancer intracellular apoptosis. [Nat. Chem. Biol. 2014, 10:9-17; Life Sciences 2006, 4] CH-j can release slight NO in cancer cells by Cope elimination reaction, and no in normal cells. NO is a gas signal molecule that calls immune cells recognized and killed cancer cells with synergistic cancer therapy. [Angew Chem, doi: 10.1002/anie.201800594; doi:10.1002/anie.201610682]. CH-j also can inhibit NaOCl with cell necrosis.

Figure 8:
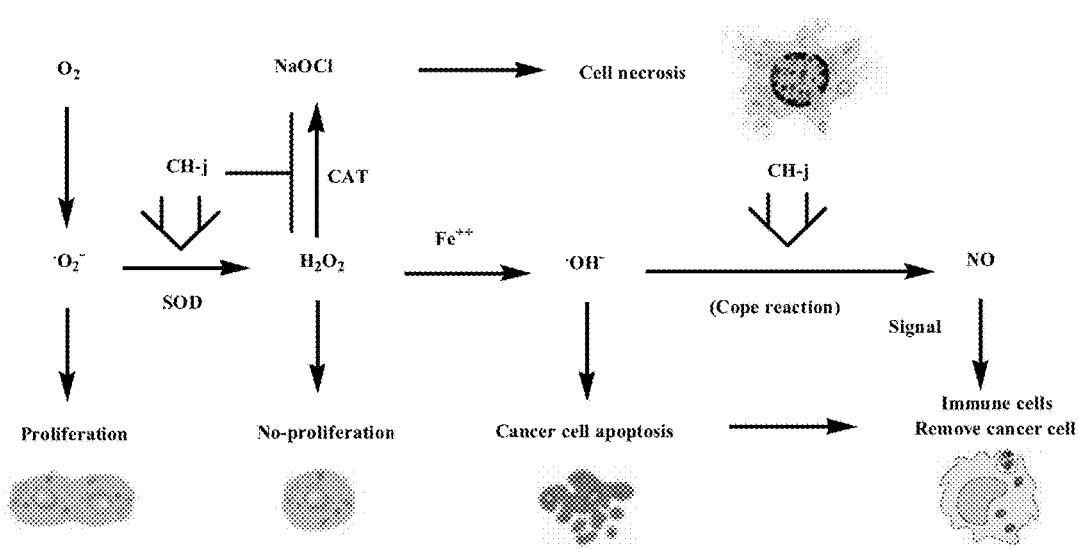

Brief summary, CH-j by capturing $.O_2^-$, releasing higher levels of $H_2O_2$, $.OH^-$ and NO in cancer cells and no in normal cells, and inhabiting NaOCl, so that is an important reason for CH-j selectively inducing solid tumor cells apoptosis and protecting normal cells. CH-j is different from the cytotoxic drugs as HCPT with damaging cancer cells and also normal cells by activating intracellular mitochondria apoptosis pathway and extrinsic death receptor pathway, due to increase the level of intracellular ROS ($.O_2^-$, $H_2O_2$, NO, $.OH^-$ and NaOCl). FIG. 8: The action mechanism of CH-j by regulating intracellular ROS in cancer cells cancer cells.

The team of Carole Nicco from France's Fifth University confirmed that the antioxidant enzymes in the elimination of $H_2O_2$, GSH pathway in the transformed cells control plays a major role in the formation of $H_2O_2$, but GSH in cancer cells produce control of $H_2O_2$ is negligible. Therefore, in normal cells, ROS is at a very low level, from NADPH, and $H_2O_2$ concentration is regulated by glutathione system. Conversely, in cancer cells, the high level of $H_2O_2$, which is more closely related to cytotoxicity, is produced through the mitochondrial respiratory chain, where the level of $H_2O_2$ is controlled by CAT. Therefore, for the first time, the group proposed that any substance that increases the level of $H_2O_2$ in the cell can reduce the proliferation of cancer and eventually lead to apoptosis. Conversely, any substance that lowers the levels of $H_2O_2$ in the cell can promote cancer growth. Therefore, the drug that can specifically improve the $H_2O_2$ in cancer cells has selective induction of cancer cell apoptosis. [Biomedicine & Pharmacotherapy, 2005, 59:169-174.]

The team of Miguel from Seville University Spain provided that the increase in the levels of $H_2O_2$ in the cells of is an important event in cancer treatment. High levels of $H_2O_2$ in cells not only inhibit the survival of cancer cells, but also induce cell apoptosis to be more sensitive than normal cells. Any drug or strategy that increases intracellular $H_2O_2$ to adequate levels can selectively induce apoptosis and result in efficacy. It is important to improve the level of $H_2O_2$ in cells, which is the key to the efficacy of anticancer drugs. [Cancer Letters, 2007, 252:1-8.]

Figure 9:
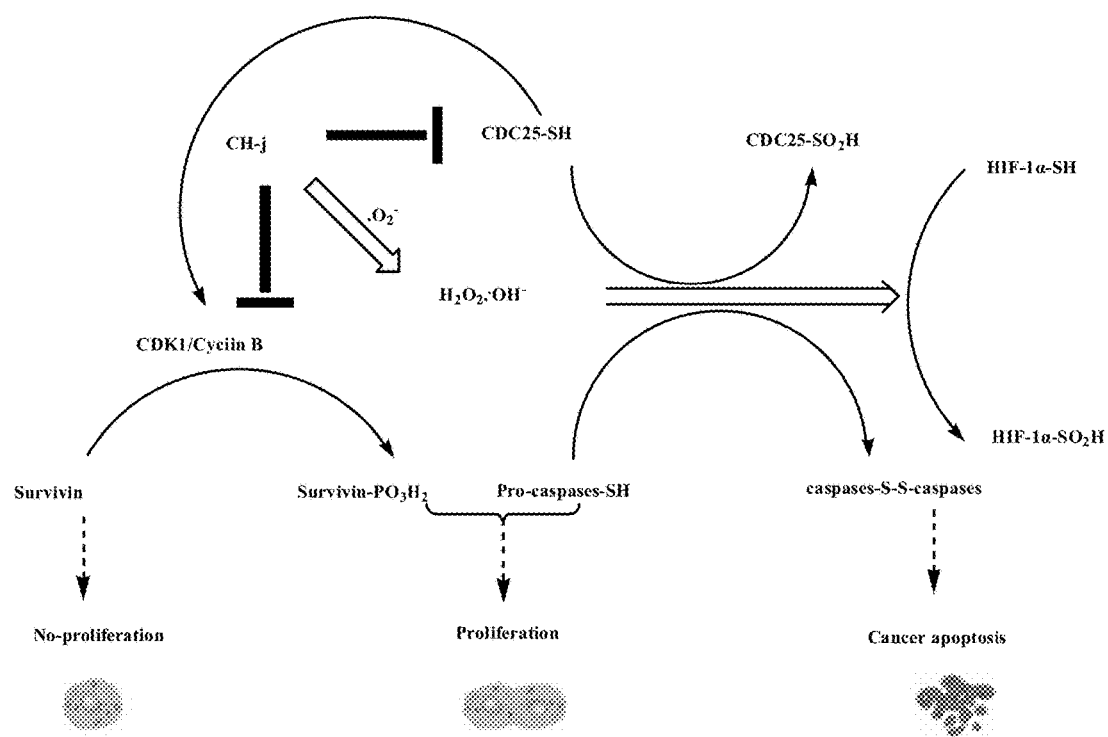

FIG. 9: The molecular biology mechanism of CH-j selectively inducing apoptosis of cancer cells.

In conclusion, the acetyl Chrysin Mannich base derivatives are a kind of CDK1 selective inhibitor. Base on the levels of $.O_2^-$ and $Fe^{++}$ are higher in cancer cells than in normal cells, the action mechanism of the acetyl Chrysin Mannich base derivatives by regulating intracellular ROS, is activating mitochondria apoptosis pathway without the death receptor pathway, thus selectively inducing apoptosis, inhibiting proliferative and metastasis of solid cancer cells and protecting normal cells. Inside, CH-j has a good druggability for the selectivity of solid cancers. Moreover, CH-f has also a good druggability for the systemic cancers.

Compared with Existing Technologies, the Advantages of this Invention are:

The acetyl Chrysin Mannich base derivatives are 2 times stronger action for CDK1 inhibition and the selective induction of apoptosis than BA-j. Inside, CH-j has a good druggability for the selectivity of solid cancers. Moreover, CH-f has also a good druggability for the systemic cancers. (BA-j is main selectivity for the blood system). The present invention provided the acetyl Chrysin Mannich base derivatives, which were different from other literature of Chrysin derivatives. So, the introduction of the acetyl to improve anticancer activity plays a key role. Due to format the stable six-member ring structure by intermolecular hydrogen bonds between phenolic hydroxyl and acetyl or Mannich amine, the "liver firs effect" and "hepatoenteral circulation" are effective inhibited with improving bioavailability significantly, and druggability more excellent.

FIGURE DESCRIPTION

FIG. 1-1: The Mannich base derivatives of acetyl Chrysin to Hep G2 in the levels of $H_2O_2$: the influence of the abscissa Mannich bases derivatives of acetyl Chrysin, X-coordinate is the test concentration of Mannich base derivatives of acetyl Chrysin (μm) for 4 h, and Y-coordinate producing $H_2O_2$ levels in cells (μM) with PF1-$H_2O_2$ 10 μM by Fluorescence Microplater Reader (488 nm/525 nm).

FIG. 1-2: The effect of CH-j/BA-j to Hep G2 and BGC-382 in the levels of $H_2O_2$: in which the X-coordinate is the concentration of CH-j/BA-j concentration (μM), and Y-coordinate is the intracellular levels of $H_2O_2$ (μM) for 4 h with PF1-$H_2O_2$ 10 μM by Fluorescence Microplater Reader (488 nm/525 nm).

FIG. 1-3: CH-j/BA-j affects the levels of $H_2O_2$ in blood cells, X-coordinate is the concentration of CH-j/BA-j concentration (μM), and Y-coordinate the intracellular levels of $H_2O_2$ (μM) for 4 h with PF1-$H_2O_2$ 10 μM by Fluorescence Microplater Reader (488 nm/525 nm).

FIG. 1-4: The performed fluorescence imaging with PF1-$H_2O_2$ 10 μM is that CH-j 12.5 μM affected the level of $H_2O_2$ for 4 h in MCF-7, GBC-823, Hep G2 and Liver by Fluorescence microscopy (488/525 nm).

FIG. 1-5: The performed fluorescence imaging with CCy-OH 10 μM is that 12.5 μM of CH-j and CH-f affected the level of .OH⁻ for 5 h in HepG2 and LO2 by Single beam electron confocal fluorescence microscope (488/604 nm).

FIG. 1-6: The performed fluorescence imaging with Rh—NO 5 μM, and add 25 μM of CH-j and CH-f for 12, 24, 48 h, affected the level of NO for 12, 24 and 48 h in MCF-7 and COS-7 by Single beam electron confocal fluorescence microscope (488/604 nm).

FIG. 2: The initial screening results of the anticancer activity of BGC-823 (MTT, for 48 h), and X-coordinate is the drug concentration (MTT, for 48 h), and Y-coordinate the cell survival rate (%) in vitro.

FIGS. 3-1 to 3-4: the detection results of cancers apoptosis were treated with 0 (A), 5(B, E), 10(C, F), 20 μM (D, G) of CH-f and CH-j for 24 h, is respectively represented.

FIG. 3-1 Hoechst 33258 staining results for MCF-7.

FIG. 3-2 PI staining results for BGC-823.

FIG. 3-3 Annexin V-FITC/PI staining results for BGC-823.

FIG. 3-4: caspases: X-coordinate is CH-j concentration (μM) and Y-coordinate the activity of caspase (%) for BGC-823.

FIG. 4: CH-j effect on the HIF-1 of BGC-823 was treated with 0, 2.5, 5, 10 μM CH-j for 1 h, then added 0.2 μM insulin culture for 24 h, and the HIF-1α and HIF-1β were determined by the immune imprinting method.

FIG. 5: The concentration of urine drug concentration-time curve in monkey (n=6) by CH-j oral 5 mg/kg, X-coordinate is oral CH-j time (h) and Y-coordinate is the concentration of CH-j (μM).

FIG. 6: 2 h distribution of the drug (100 mg/kg) by CH-j rats: Y-coordinate is the concentration of CH-j (μg/g), by intravenous (i.v.), by oral (p.o.).

FIG. 7: H-460 carcinoma in male BALB/c nude mice xenograft model, two times a day to fill the stomach to CH-j 5 and 10 mg/kg, for 10 days in a row, X-coordinate is experimental time (days), and Y-coordinate vertical volume of H-460 carcinoma (mm³).

FIG. 8: The action mechanism of CH-j by regulating intracellular ROS in cancer cells cancer cells.

FIG. 9: The molecular biology mechanism of CH-j selectively inducing apoptosis of cancer cells.

EXAMPLES

The following unrestricted implementation example is used to further this invention, Mannich bases derivatives of acetyl Chrysin, its preparation method and application, but should be clear, belong to the substituent of alternative schemes, is not limited to implement and described in the case of these cycloalkylamine-methyl, and these instances should not be interpreted as any form of invention.

Example 1

6-Acetyl-5, 7-dihydroxy-8-(4-hydroxy-piperidin-1-ylmethyl)-2-phenyl-chromen-4-one [CH-j]

The mixture of 6-acetyl-Chrysin (CH of purity 95.3%) 50 g and ethyl acetate 2 L was stirred and heated to reflux, then added formaldehyde solution and 4-hydroxypiperidine 1:1.5:1.5 (M) and stirred for 3 h. The precipitate was removed by filtration, washed with ethyl acetate, dried under reduced pressure at 60° C., to get the product as yellow solid 60.5 g of purity 99.1%, and to get the yellow column crystal of purity 99.5% by recrystallization. It is purple-red in ferric chloride solution. [α]+2450° (25° C. methanol). MS (API-ESI) m/z: [M+H]⁺ 410, [M+H-101]⁺ 309. HR-MS (API-ESI) m/z: [M–H]⁻ 408.1444 (calculated 408.1447), $C_{23}H_{23}NO_6$, WT409.43. UV: 5 μg/1 ml methanol, $E^{1\%}_{1cm}$ (λmax 283 nm) 1044. IR (KBr, cm⁻¹): 3513 (ν Ph-OH weak), 3063 ($CH_3$), 1658 (ν C=O), 1625 ($CH_3$—C=O), 1587, 1449, 1379, 777, 687. ¹H-NMR (DMSO-d₆, 500 MHz) δ: 8.03 (d, 2H, Ph-2', 6'-H), 7.57 (m, 3H, Ph-3', 4', 5'-H), 6.83 (s, 1H, 3-H), 3.97 (s, 2H, C8-$CH_2$), 3.63 m, 1H, CH—OH), 3.06-2.64 (m, 4H, 2", 6"-$CH_2$), 2.50 (—$CH_3$), 1.83-1.49 (m, 4H, 3", 5"-$CH_2$). ¹³C-NMR (DMSO-d6/$CH_3SO_3H$, 500 MHz) δ: 204.6 (C=O), 182.8 (C-4), 168.3 (C-7), 167.7 (C-9), 164.2 (C-2), 159.2 (C-5), 132.7 (C-1'), 129.9 (C-4'), 129.3 (C-3', 5'), 127.0 (C-2', 6'), 105.9 (C-6), 105.5 (C-8), 103.2 (C-10), 96.1 (C-3).

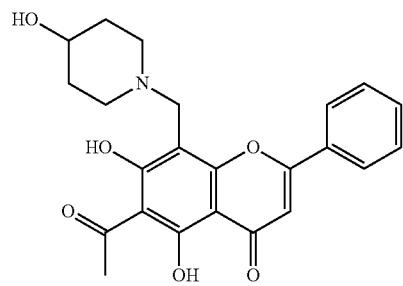 [SMILES: CC(=O)c1c(O)c(CN2CCC(O)CC2)c2oc(-c3ccccc3)cc(=O)c2c1O]

Example 2

6-Acetyl-5,7-dihydroxy-8-[4-(2-hydroxy-ethyl)-piperazin-1-ylmethyl]-2-phenyl-chromen-4-one [CH-i]

The mixture of 6-acetyl-Chrysin (CH of purity 95.3%) 10 g and ethyl acetate 500 ml was stirred and heated to reflux, then added formaldehyde solution and 4-hydroxyethyl-piperazine 1:1.5:1.5 (M), and stirred for 1.5 h. The precipitate was removed by filtration, washed with ethyl acetate, dried under reduced pressure at 60° C., to get the product as yellow solid 7.5 g of purity 99.2%. It is purple-red in ferric chloride solution. MS (API-ESI) m/z: [M+H]⁺ 439, $C_{24}H_{26}N_2O_6$. UV: 5 μg/1 ml methanol, $E^{1\%}_{1cm}$ (λmax 286 nm) 1016. IR (KBr, cm⁻¹): 3486 (νOH), 2934 (ν $CH_3$), 1651 (ν C=O), 1624 (ν $CH_3$—C=O), 1587, 1446, 845, 773. ¹H-NMR (500 MHz, DMSO-d₆) δ: 8.11 (d, 2H, Ph-2', 6'-H), 7.62 (m, 3H, Ph-3', 4', 5'-H), 7.05 (s, 1H, 3-H), 3.88 (s, 2H, 8-$CH_2$), 3.47 (t, J=6.2 Hz, 2H, 8-$CH_2OH$), 2.68-2.66 (m, 4H, 2", 3", 4", 5"-H), 2.61 (s, 3H, $CH_3$), 2.40 (t, J=6.1 Hz, 2H, 7"-H).

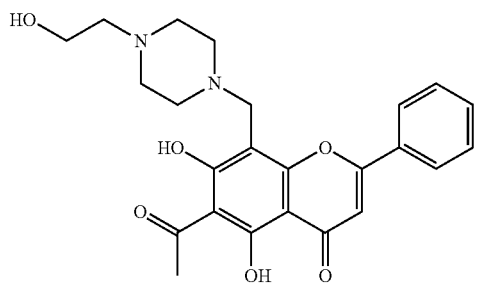 [SMILES: CC(=O)c1c(O)c(CN2CCN(CCO)CC2)c2oc(-c3ccccc3)cc(=O)c2c1O]

Example 3

6-Acetyl-5, 7-dihydroxy-8-(2-hydroxymethyl-pyrrolidin-1-ylmethyl)-2-phenyl-chromen-4-one [CH-h]

The mixture of 6-acetyl-Chrysin (CH of purity 95.3%) 10 g and ethyl acetate 500 ml was stirred and heated to reflux, then added formaldehyde solution and L-prolinol 1:1.5:1.5 (M), and stirred for 2.5 h. The precipitate was removed by filtration, washed with ethyl acetate, dried under reduced pressure at 60° C., to get the product as yellow solid 2.4 g, and to get the yellow column crystal of purity 95.5% by recrystallization. It is purple-red in ferric chloride solution. MS (API-ESI) m/z: [M+H]$^+$ 410, [M−H]$_−$ 408. $C_{23}H_{23}NO_6 \cdot H_2O$. UV: 5 μg/1 ml methanol, $E^{1\%}_{1cm}$ (λmax 282 nm) 968. IR (KBr, cm$^{-1}$): 3306 (ν OH), 2951 (ν CH$_3$), 1651 (ν C=O), 1625 (ν CH$_3$—C=O), 1589, 1451, 771, 686. $^1$H-NMR (500 MHz, DMSO-d$_6$) δ: 8.07 (dd, Ph-2', 6'-H), 7.59 (m, Ph-3', 4', 5'-H), 6.82 (s, 1H, 3-H), 4.41-4.25 (dd, J=13.4 Hz, 2H, 8-CH$_2$), 3.71-3.63 (dd, J=11.7, 5.3 Hz, 2H, 6"-H), 3.53 (H$_2$O), 3.40 (m, 1H, 5"-H), 3.19 (m, 1H, 2"-H), 2.95 (m, 1H, 2"-H), 2.46 (s, 3H, COCH$_3$), 2.06 (m, 1H, 4"-H), 1.88 (m, 1H, 3"-H), 1.75 (m, 2H, 3", 4"-H).

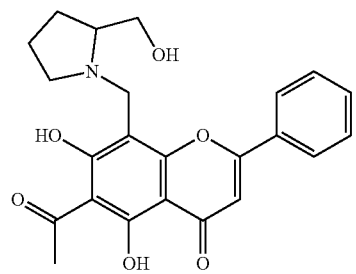 [SMILES: CC(=O)c1c(O)c(CN2CCCC2CO)c2oc(-c3ccccc3)cc(=O)c2c1O]

Example 4

6-Acetyl-5, 7-dihydroxy-8-morpholin-4-ylmethyl-2-phenyl-chromen-4-one [CH-d]

The mixture of 6-acetyl-Chrysin (CH of purity 95.3%) 10 g and dioxane 200 ml was stirred and heated at 95° C., then added formaldehyde solution and morpholine 1:1.5:1.5 (M), and stirred for 2.5 h. The precipitate was removed by filtration, washed with ethyl acetate, dried under reduced pressure at 60° C., to get the product as yellow solid 9.2 g, and to get the yellow column crystal of purity 99.8% by recrystallization. It is purple-red in ferric chloride solution. MS (API-ESI) m/z: [M+H]$^+$ 396, $C_{22}H_{21}NO_6$. UV: 5 μg/1 ml methanol, $E^{1\%}_{1cm}$ (λmax 286 nm) 1129. IR (KBr, cm−1): 3307 (ν OH), 2953 (ν CH$_3$), 1647 (ν C=O), 1630 (ν CH3-C=O), 1587, 1451, 771, 694. $^1$H-NMR (500 MHz, DMSO-d$_6$) δ: 8.14 (d, Ph-2', 6'-H), 7.64 (m, Ph-3', 4', 5'-H), 7.15 (s, 1H, 3-H), 3.79 (s, 2H, 8-CH$_2$), 3.57 (m, 2H, 3", 5"-H), 2.69 (s, 3H, COCH$_3$), 2.55 (m, 2H, 2", 6"-H).

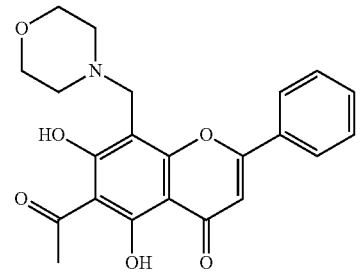 [SMILES: CC(=O)c1c(O)c(CN2CCOCC2)c2oc(-c3ccccc3)cc(=O)c2c1O]

Example 5

6-Acetyl-5, 7-dihydroxy-2-phenyl-8-(thiomorpholin-4-ylmethyl)-2-phenyl-chromen-4-one [CH-e]

The mixture of 6-acetyl-Chrysin (CH of purity 95.3%) 10 g and acetyl acetone 200 ml was stirred and heated at 95° C., then added formaldehyde solution and sulfurmorpholine 1:2:2 (M), and stirred for 2.5 h. The precipitate was removed by filtration, washed with ethyl acetate, dried under reduced pressure at 60° C., to get the product as yellow solid 10.3 g of purity 95.4%. It is purple-red in ferric chloride solution. MS (API-ESI) m/z: [M+H]$^+$ 412, $C_{22}H_{21}NO_5S$. UV: 5 μg/1 ml methanol, $E^{1\%}_{1cm}$ (λmax 286 nm) 1133. IR (KBr, cm$^{-1}$): 3467 (ν OH), 2908 (ν CH$_3$), 1647 (ν C=O), 1626 (ν CH$_3$—C=O), 1587, 1441, 777, 688. $^1$H-NMR (500 MHz, DMSO-d$_6$) δ: 8.13 (m, Ph-2', 6'-H), 7.64 (m, Ph-3', 4', 5'-H), 7.14 (s, 1H, 3-H), 3.82 (s, 2H, 8-CH$_2$), 2.82 (m, 2H, 2", 6"-H), 2.68 (s, 3H, CH$_3$), 2.62 (m, 2H, 3", 5"-H).

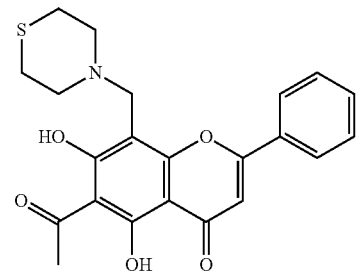

Example 6

6-Acetyl-5, 7-dihydroxy-8-(4-methylpiperazin-1-ylmethyl)-2-phenyl-chromen-4-one [CH-f]

The mixture of 6-acetyl-Chrysin (CH of purity 95.3%) 10 g and ethyl acetate 500 ml was stirred and heated to reflux, then added formaldehyde solution and 4-methylpiperazine 1:1.5:1.5 (M), and stirred for 1.5 h. The precipitate was removed by filtration, washed with ethyl acetate, dried under reduced pressure at 60° C., to get the product as yellow solid 7.1 g of purity 99.8%. It is purple-red in ferric chloride solution. MS (API-ESI) m/z: [M+H]$^+$ 409, $C_{22}H_{21}NO_5S$. It was added methylsulfonyl in ethyl acetate, precipitate removed by filtration, washed with ethyl acetate, dried under reduced pressure at 80° C., to get the product with yellow solid. $^1$H-NMR (500 MHz, DMSO-d$_6$, CH$_3$SO$_3$H) δ: 8.21 (m, Ph-2', 6'-H), 7.66 (m, Ph-3', 4', 5'-H), 7.31 (s, 1H, 3-H), 4.47 (s, 2H, 8-CH$_2$), 3.65-3.24 (m, 8H, CH$_2$2", 3", 4", 5"-H), 2.86 (s, 3H, N—CH$_3$), 2.78 (s, 3H, COCH$_3$).

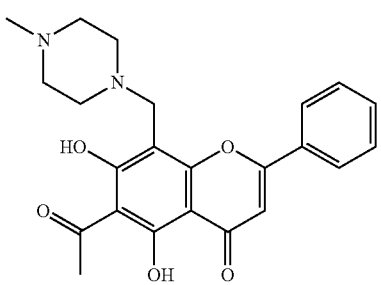 [SMILES: CC(=O)c1c(O)c(CN2CCN(C)CC2)c2oc(-c3ccccc3)cc(=O)c2c1O]

Example 7

6-Acetyl-5, 7-dihydroxy-2-phenyl-8-(piperidin-1-ylmethyl)-2-phenyl-chromen-4-one [CH-c]

The mixture of 6-acetyl-Chrysin (CH of purity 95.3%) 10 g and ethyl acetate 500 ml was stirred and heated to reflux, then added formaldehyde solution and piperidine 1:1.5:1.5 (M), and stirred for 1.5 h. The precipitate was removed by filtration, washed with ethyl acetate, dried under reduced pressure at 60° C., to get the product as yellow solid 9.2 g of purity 99.5%. It is purple-red in ferric chloride solution. MS (API-ESI) m/z: [M+H]$^+$ 394, $C_{22}H_{23}NO_6$. $^1$H-NMR (DMSO-d6, 500 MHz) δ: 8.07 (d, 2H, Ph-2', 6'-H), 7.60 (m, 3H, Ph-3', 4', 5'-H), 6.89 (s, 1H, 3-H), 4.14 (s, 2H, C8-CH$_2$), 2.95 (s, 2H, COCH$_3$), 1.64-1.23 (m, 10H, 2", 3", 4", 5", 6"-CH$_2$).

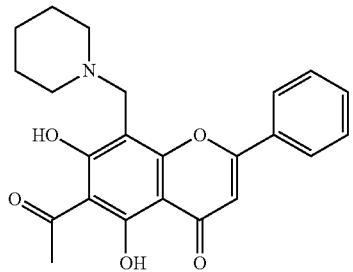 [SMILES: CC(=O)c1c(O)c(CN2CCCCC2)c2oc(-c3ccccc3)cc(=O)c2c1O]

Example 8

8-Acetyl-5,7-dihydroxy-6-(4-hydroxy-piperidin-1-ylmethyl)-2-phenyl-chromen-4-one [8-(1-hydroxy-vinyl)-Chrysin, is-CH-j]

The mixture of 8-(1-hydroxy-vinyl)-Chrysin (contents 60.0%) 13 g and ethyl acetate 500 ml was stirred and heated to reflux, then added formaldehyde solution and 4-hydroxy-piperidine 1:1.5:1.5 (M), and stirred for 1 h. The precipitate was removed by filtration, washed with ethyl acetate, dried under reduced pressure at 60° C., to get the product as yellow solid 5.3 g of purity 82.5%, and to get the yellow column crystal of purity 97.0% by recrystallization. It is orange-red in ferric chloride solution. [α]+2450° (25° C. methanol). MS (API-ESI) m/z: [M+H]$^+$ 410, [M+H-101]$^+$ 309, [M-H]$^-$ 408. HR-MS (API-ESI) m/z: [M-H]$^-$ 408.1444 (calculated 408.1447), $C_{23}H_{23}NO_6$, WT409.43. UV: 5 μg/1 ml methanol, $E^{1\%}_{1cm}$ (λmax 255 nm) 878. IR (KBr, cm$^{-1}$): 3349 (ν CH$_2$=COH), 1646 (ν C=O), 1599, 1578, 1549, 769, 682. $^1$H-NMR (DMSO-d$_6$, 500 MHz) δ: 8.12 (d, 2H, Ph-2', 6'-H), 7.56 (m, 3H, Ph-3', 4', 5'-H), 6.88 (s, 1H, 3-H), 4.07 (s, 2H, C6-CH$_2$), 3.77 (m, 1H, CH—OH), 2.99-3.25 (m, 4H, 2", 6"-CH$_2$), 2.52 (s, 3H, CH$_3$), 1.65-1.95 (m, 4H, 3", 5"-CH$_2$). $^{13}$C-NMR (DMSO-d$_6$, 400 MHz) δ: 198.1 (C=O), 180.3 (C-14) 75.6 (C-7), 161.3 (C-5), 161.2 (C-2), 157.0 (C-9), 131.5 (C-1'), 131.0 (C-4'), 128.9 (C-3', 5'), 126.2 (C-2', 6'), 109.4 (C-8), 104.4 (C-6), 102.3 (C-3), 98.6 (C-10). UV max 255 nm (CH-j 283 nm); $^{13}$C-NMR 104.4 (C-6) and 109.4 (C-8) (CH-j 105.9 (C-6) and 105.5 (C-8)).

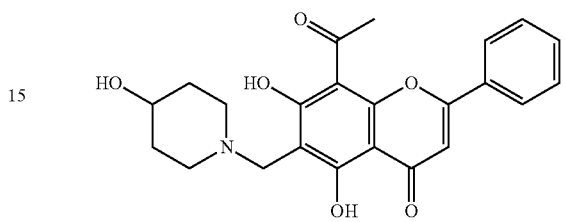

Example 9

6-Acetyl-5, 7-dihydroxy-2-phenyl-4H-chromen-4-one [6-acetyl-Chrysin]

The mixture of 2, 4, 6-three-hydroxy-acetophenone monohydrate 150 g, get a pale orange yellow needle crystal 155 g of purity 95.3% by according to the synthesis of 6-acetyl-Chrysin [J. Chem. Soc. Perkin Trans I, 1973, 503-505], and to get the light yellow crystalline filaments of purity 99.3% by recrystallization with DMF. It is purple-red in ferric chloride solution. MS (API-ESI) m/z: [M+H]$^+$ 297, [M–H]$^-$ 295, $C_{17}H_{12}O_5$. UV: 5 μg/1 ml methanol, $E^{1\%}_{1cm}$ (λmax 283 nm) 1532. IR (KBr, cm$^{-1}$): 3063 (νCH3), 1646 (C=O), 1586, 1452, 1379, 1178, 767, 682. $^1$H-NMR (DMSO-d$_6$, 500 MHz) δ: 8.03 (d, 2H, Ar-2', 6'-H), 7.62 (m, 3H, Ar-3', 4', 5'-H), 7.10 (s, 1H, 3-H), 6.63 (s, 1H, 8-H), 2.74 (s, CH$_3$).

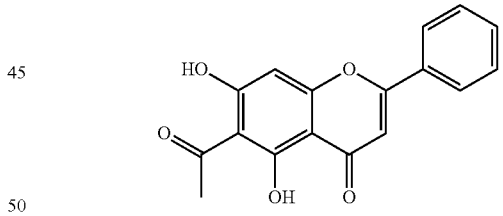

Example 10

8-Acetyl-5,7-dihydroxy-2-phenyl-chromen-4-one [8-Acetyl-Chrysin]

The solution after the separation of 6-acetyl-Chrysin was distilled to recover the part of solvent, precipitate was removed by filtration, washed with ethyl acetate, dried under reduced pressure at 60° C., to get the product as pale orange-yellow crystals (is-CH of purity 60.0%), by flash chromatography of silica gel with petroleum ether-ethyl acetate-chloroform (40:15:3) as mobile phase, and to get the product as almost white crystalline of purity 95.0%. It is orange-red in ferric chloride solution. MS (API-ESI) m/z: [M+H]$^+$ 297, [M–H]$^-$ 295, $C_{17}H_{12}O_5$. UV: λmax 276 nm (methanol). IR (KBr, cm$^{-1}$): 3440 (ν CH$_2$=COH), 2253, 2126, 1658 (ν C=O). $^1$H-NMR (DMSO-d$_6$, 500 MHz) δ: 8.08 (d, Ar-2H, 2', 6'-H), 7.63 (m, Ar-3H, 3', 4', 5'-H), 7.13 (s, 1H, 3-H), 6.36 (s, 1H, 6-H), 2.77 (s, CH$_3$).

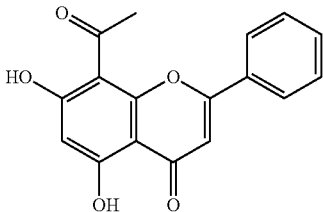 [SMILES: CC(=O)c1c(O)cc(O)c2c(=O)cc(-c3ccccc3)oc12]

We claim:

1. A series of acetyl Chrysin Mannich base derivatives with the structures illustrated in the following scheme: wherein R$_1$ is CH$_3$CO and R$_2$ is cycloalkylamine-methyl, or wherein R$_1$ is cycloalkylamine-methyl and R$_2$ is CH$_3$CO, only one is CH$_3$CO in R$_1$ or R$_2$; wherein the cycloalkylamine-methyly is pyrrolidinylmethyl, piperidinylmethyl, N-morpholinylmethyl, N-thiomorpholinylmethyl, N-methylpiperazinylmethyl, piperazinylmethyl, N-2'-hydroxyethylpiperazinylmethyl, 4'-piperidonylmethyl, 4'-hydroxypiperidinyl methyl, 3'-hydroxypyrrolidinylmethyl, L-prolinolmethyl or D-prolinolmethyl.

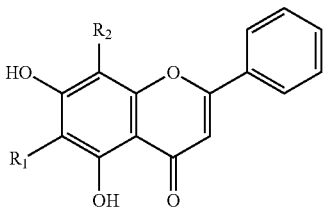

2. The acetyl Chrysin Mannich base derivatives of claim 1, wherein R$_1$ is CH$_3$CO and R$_2$ is 4'-hydroxylpiperidinylmethyl, N-morpholinylmethyl, N-thiomorpholinylmethyl, N-2'-hydroxyethylpiperazinylmethyl, N-methylpiperazinylmethyl, piperidinylmethyl or L-prolinolmethyl.

3. The acetyl Chrysin Mannich base derivatives of claim 1, wherein R$_2$ is CH$_3$CO and R$_1$ is 4'-hydroxylpiperidinylmethyl, N-morpholinylmethyl, N-thiomorpholinylmethyl, N-2'-hydroxyethylpiperazinylmethyl, N-methylpiperazinylmethyl, piperidinylmethyl or L-prolinolmethyl.

4. The acetyl Chrysin Mannich base derivatives of claim 1, wherein R$_1$ is CH$_3$CO and R$_2$ is 4'-hydroxylpiperidinylmethyl, N-morpholinylmethyl, N-thiomorpholinylmethyl, N-2'-hydroxyethylpiperazinylmethyl or N-methylpiperazinylmethyl; or wherein R$_2$ is CH$_3$CO and R$_1$ is 4'-hydroxylpiperidinylmethyl, N-morpholinylmethyl, N-thiomorpholinylmethyl, N-2'-hydroxyethylpiperazinylmethyl or N-methylpiperazinylmethyl.

5. A process of acetyl Chrysin Mannich base derivatives of claim 1 wherein the steps are as follows: to take 6-acetyl-Chrysin [6-acetyl-5, 7-dihydroxy-8-(4-hydroxy-piperidin-1-ylmethyl)-2-phenyl-chromen-4-one] or 8-acetyl-Chrysin [8-acetyl-5, 7-dihydroxy-6-(4-hydroxy-piperidin-1-ylmethyl)-2-phenyl-chromen-4-one] as lead compound, mixed it with formaldehyde solution and a cycloalkylamine compound in an organic solution, stirring and heat by Mannich reaction, filter, wash, and dry, so as to get the product with a content of not less than 98% (weight).

6. The process of claim 5, wherein the organic solution is ethanol, acetonitrile, tetrahydrofuran, dioxane, ethyl-acetate, butyl-acetate, acetyl-acetone, ethyl-acetoacetate or methyl-isobutyl-ketone, or mixture.

7. The process of claim 5, wherein the cycloalkylamine compound is pyrrolidine, piperidine, morpholine, sulfurmorpholine, 4-methylpiperazine, piperazine, 4-hydroxyethyl-piperazine, 4-piperidone, 4-piperidinol, 3-pyrrolidinol, L-prolinol or D-prolinol.

8. The acetyl Chrysin Mannich base derivatives of claim 2, wherein R$_1$ is CH$_3$CO and R$_2$ is 4'-hydroxylpiperidinylmethyl or N-methylpiperazinylmethyl.

9. The acetyl Chrysin Mannich base derivatives of claim 4, wherein R$_2$ is CH$_3$CO and R$_1$ is 4'-hydroxylpiperidinylmethyl or N-methylpiperazinylmethyl.

10. A composition comprising an acetyl Chrysin Mannich base derivative according to claim 1.

11. A composition comprising an acetyl Chrysin Mannich base derivative according to claim 2.

12. A composition comprising an acetyl Chrysin Mannich base derivative according to claim 3.

13. A composition comprising an acetyl Chrysin Mannich base derivative according to claim 4.

14. A composition comprising an acetyl Chrysin Mannich base derivative according to claim 7.

15. A composition comprising an acetyl Chrysin Mannich base derivative according to claim 8.

* * * * *